(12) United States Patent
Downie et al.

(10) Patent No.: US 11,397,145 B2
(45) Date of Patent: Jul. 26, 2022

(54) DIAGNOSTIC METHODS AND DEVICE

(71) Applicants: ROYAL MELBOURNE INSTITUTE OF TECHNOLOGY, Victoria (AU); THE UNIVERSITY OF MELBOURNE, Victoria (AU)

(72) Inventors: Laura Elizabeth Downie, Victoria (AU); Leslie Yeo, Victoria (AU); Amarin George McDonnell, Victoria (AU)

(73) Assignees: THE UNIVERSITY OF MELBOURNE, Victoria (AU); ROYAL MELBOURNE INSTITUTE OF TECHNOLOGY, Victoria (AU)

( * ) Notice: Subject to any disclaimer, the term of this patent is extended or adjusted under 35 U.S.C. 154(b) by 374 days.

(21) Appl. No.: 16/327,063

(22) PCT Filed: Aug. 24, 2017

(86) PCT No.: PCT/AU2017/050900
§ 371 (c)(1),
(2) Date: Feb. 21, 2019

(87) PCT Pub. No.: WO2018/035569
PCT Pub. Date: Mar. 1, 2018

(65) Prior Publication Data
US 2020/0158611 A1  May 21, 2020

(30) Foreign Application Priority Data
Aug. 24, 2016  (AU) .............................. 2016903362

(51) Int. Cl.
*G01N 11/02* (2006.01)
*G01N 33/487* (2006.01)
(Continued)

(52) U.S. Cl.
CPC ............ *G01N 11/02* (2013.01); *A61B 5/0051* (2013.01); *A61B 8/00* (2013.01); *G01N 13/02* (2013.01);
(Continued)

(58) Field of Classification Search
CPC .... G01N 11/02; G01N 29/2418; G01N 29/00; G01N 29/022; G01N 29/14;
(Continued)

(56) References Cited

U.S. PATENT DOCUMENTS

| 2011/0224190 A1* | 9/2011 | Huang | A61P 11/00 544/405 |
| 2013/0233059 A1* | 9/2013 | McDonnell | G01N 11/00 73/54.04 |

(Continued)

FOREIGN PATENT DOCUMENTS

| JP | 2009-535620 A | 11/2007 |
| JP | 2012-531595 A | 12/2012 |

(Continued)

OTHER PUBLICATIONS

Tiffany, John M. "The viscosity of human tears." International ophthalmology 15.6 (1991): 371-376. (Year: 1991).*
(Continued)

*Primary Examiner* — Herbert K Roberts
*Assistant Examiner* — Fatemeh Esfandiari Nia
(74) *Attorney, Agent, or Firm* — Neal, Gerber & Eisenberg LLP

(57) ABSTRACT

A method for evaluating Dry Eye Disease ("DED") in a human or animal subject is provided. Thread thinning dynamics of a tear sample of the subject are determined using an acoustically-driven microfluidic extensional rheometry instrument. At least one physical parameter value of the tear sample is calculated based at least in part on the
(Continued)

determined thread thinning dynamics. DED is evaluated based at least in part on the at least one calculated physical parameter value of the tear sample. A device for evaluating Dry Eye Disease (DED) in a human or animal subject is also provided. The device includes an acoustically-driven microfluidic extensional rheometry instrument and a processing device configured to evaluate DED based at least in part on the calculated at least one physical parameter value of the tear sample.

20 Claims, 14 Drawing Sheets

(51) Int. Cl.

| | | |
|---|---|---|
| *G01N 29/14* | (2006.01) | |
| *G01N 29/02* | (2006.01) | |
| *G01N 29/24* | (2006.01) | |
| *A61B 5/00* | (2006.01) | |
| *G01N 13/02* | (2006.01) | |
| *G01N 29/00* | (2006.01) | |
| *A61B 8/00* | (2006.01) | |

(52) U.S. Cl.
CPC ............ *G01N 29/00* (2013.01); *G01N 29/022* (2013.01); *G01N 29/14* (2013.01); *G01N 29/2418* (2013.01); *G01N 33/487* (2013.01)

(58) Field of Classification Search
CPC ............. G01N 29/036; G01N 29/4436; G01N 2291/02827; G01N 13/02; G01N 33/487; G01N 2011/0073; A61B 5/0051; A61B 8/00
See application file for complete search history.

(56) References Cited

U.S. PATENT DOCUMENTS

| | | | | |
|---|---|---|---|---|
| 2014/0129259 A1* | 5/2014 | Seriani | ................... | G16H 50/20 705/3 |
| 2018/0050074 A1* | 2/2018 | Whitcup | ................ | A61K 47/38 |
| 2019/0275089 A1* | 9/2019 | Pintor Just | ............ | A61K 9/127 |

FOREIGN PATENT DOCUMENTS

| | | |
|---|---|---|
| WO | WO 2011/160168 | 12/2011 |
| WO | WO 2011/093209 A1 | 11/2012 |

OTHER PUBLICATIONS

Abelson, Mark B., et al. "Alternative reference values for tear film break up time in normal and dry eye populations." Lacrimal Gland, Tear Film, and Dry Eye Syndromes 3. Springer, Boston, MA, 2002. 1121-1125 (Year: 2002).*
Koh, Shizuka, et al. "Effects of suppression of blinking on quality of vision in borderline cases of evaporative dry eye." Cornea 27.3 (2008): 275-278 (Year: 2008).*
International Search Report for Application No. PCT/AU2017/050900 dated Nov. 1, 2017.
Notification of the Recording of a Change (PCT Rule 92bis) Form PCT/IB/306 dated Feb. 18, 2019.
Tiffany, J.M., "The viscosity of human tears," International Ophthamology, vol. 15, pp. 371-376 (1991 ).
McDonnell, A. G., "The acoustically-driven microfluidic extensional rheometer: development, validation, and application to complex low-viscosity fluids," PhD Thesis, Monash University, Feb. 23, 2016.
International-Type Search Report dated Aug. 2, 2017 for Australian Provisional Patent Application No. 2016903362.
International Preliminary report on Patentability dated Feb. 26, 2019 for International Application No. PCT/AU2017/050900.
Extended European Search Report dated Mar. 16, 2020 for European Patent Application No. 17842455.2.
Gouveia S M et al.: "Human tear viscosity: An interactive role for proteins and lipids", Biochimica et Biophysica ACTA (BBA)—Proteins & Proteomics, Elsevier, Netherlands, vol. 1753, No. 2, Dec. 1, 2005, pp. 155-163, XP027627787, ISSN: 1570-9639.
McDonnell Amarin G et al.: "ADMiER-ing thin but complex fluids", Smart Nano-Micro Materials and Devices, SPIE, 1000 20th St. Bellingham WA 98225-6705 USA, vol. 8204, No. 1, Dec. 21, 2011, pp. 1-7, XP060000517, DOI: 10.1117/12.903238.
Bhattacharjee P K et al.: "Extensional flow of low-viscosity fluids in capillary bridges formed by pulsed surface acoustic wave jetting", New Journal of Physics, Institute of Physics Publishing, Bristol, GB, vol. 13, No. 2, Feb. 1, 2011, p. 23005, XP020204377, ISSN: 1367-2630, DOI: 10.1088/1367-2630/13/2/023005.
Notification of Reasons for Rejection dated May 11, 2021 (with English translation) for Japanese Patent Application No. 2019-510809.
Communication pursuant to Article 94(3) EPC dated Aug. 10, 2021 for European Patent Application No. 17842455.2.

* cited by examiner

|  | Healthy (n = 10) | Borderline (n = 6) | Dry (n = 6) |
|---|---|---|---|
| Tear osmolarity (mOsmol/L) | 294.2 ± 1.4 | 304.9 ± 3.2* | 318.5 ± 2.4* |
| NITBUT (seconds) | 17.8 ± 1.7 | 13.6 ± 3.4 | 11.8 ± 3.0* |
| NaFl TBUT (seconds) | 11.4 ± 1.7 | 6.1 ± 0.5* | 6.4 ± 2.6* |
| Total ocular surface staining score (/15.0) | 0.8 ± 0.2 | 1.6 ± 0.2* | 1.8 ± 0.5* |
| Schirmer (mm/5min) | 17.7 ± 2.0 | 10.2 ± 2.7* | 6.5 ± 2.7* |

| | n (eyes) | Clinical dry eye severity score (/4.0) | TBUT (s) | Schirmer test (mm/5min) | Tear extensional viscosity (Pa.s) |
|---|---|---|---|---|---|
| Healthy | 22 | 0.3 ± 0.1 | 12.7 ± 6.6 | 19.0 ± 7.5 | 0.013 ± 0.005 |
| Borderline | 47 | 0.8 ± 0.2 | 7.6 ± 3.2 | 10.9 ± 6.3 | 0.012 ± 0.005 |
| Dry | 87 | 1.4 ± 0.3 | 5.7 ± 2.6 | 7.6 ± 6.0 | 0.007 ± 0.003 |
| - Aqueous | 47 | 1.4 ± 0.3 | 5.7 ± 3.1 | 4.0 ± 2.3 | |
| - Evaporative | 40 | 1.4 ± 0.3 | 5.7 ± 2.0 | 11.8 ± 6.4 | |

# DIAGNOSTIC METHODS AND DEVICE

PRIORITY CLAIM

This application is a national stage application of PCT/AU2017/050900, filed on Aug. 24, 2017, which claims the benefit of and priority to Australian Patent Application No. 2016903362, filed on Aug. 24, 2016, the entire contents of which are each incorporated by reference herein.

TECHNICAL FIELD

The present disclosure relates to a method and device configured to evaluate Dry Eye Disease (DED) in a human or animal subject. It relates more particularly but not exclusively to methods for diagnosing and monitoring DED, assessing the severity of DED and identifying clinical subtypes of DED, and a device customised for performing the diagnostic methods.

BACKGROUND

Dry Eye Disease ("DED") is a highly prevalent condition that affects the tear film and ocular surface of human or animal eyes resulting in discomfort and impaired vision.

DED is a multifactorial condition that involves perturbation(s) to the lacrimal functional unit ("LFU") consisting of the lacrimal gland and its accessory glands, ocular surface components (i.e., cornea and conjunctiva), meibomian glands, eyelids and their associated sensory and motor nerves. Under physiologic conditions, LFU regulates tear secretion, distribution and clearance, in response to endogenous and exogenous factors, to maintain ocular surface integrity. Disruption to one or more components of the LFU promotes a loss of tear homeostasis and the tear film dysfunction that characterises DED.

Tear hyperosmolarity, being a consequence of reduced lacrimal secretion and/or excessive tear evaporation, is an established feature of DED. While tear osmolarity measures were historically confined to the laboratory setting, clinical implementation has more recently been facilitated with microchip technology using the TearLab™ system. However, measurement reliability with the TearLab™ system is influenced by a range of factors, such as ambient temperature and operator error. Furthermore, the cost of the system is substantial and employs relatively expensive, single-use consumables thus limiting use in clinical practice.

In addition to elevated osmolarity, DED is associated with altered expression of ocular mucins, tear proteomic changes and structure-specific alterations to tear lipids. These changes compromise tear film function. Tear film performance is traditionally assessed clinically using 'tear break-up time' ("TBUT"), involving the instillation of sodium fluorescein ("NaFl") into the eye and observation of the tear film using a slit lamp biomicroscope through cobalt blue illumination. TBUT is recorded as the time, in seconds, between a full blink and the first appearance of a break (or dark patch) in the tears. This method of assessing tear stability has known limitations, in particular that instilling fluid into the eye disrupts tear stability. The technique also has poor reproducibility since it is influenced by a variety of factors such as pH and drop size of NaFl instilled, illumination technique and the clinician's expertise. Intrinsic factors, such as the patient's blinking characteristics (e.g., quality and completeness), may also contribute to variability in tear stability measures.

While other specialised tests, such as tear interferometry, corneal confocal microscopy and optical coherence tomography also exist to examine tear behaviour, the cost of these devices and/or complexity of their operation have limited uptake in clinical practice. An example includes the Keratograph® 5M (Oculus Inc.) which is a corneal topographer that incorporates photo- and video-imaging to provide estimates of tear stability and to enable visualisation of the lipid-producing meibomian glands. However, lack of clinical validation and objective quantitative measures have limited its use.

Clinically, DED can be sub-categorised as aqueous deficient and/or evaporative in aetiology. The former primarily involves reduced lacrimal gland secretion, whereas the latter is considered predominately due to abnormalities in the lipid-secreting meibomian glands. Clinicians face a further clinical challenge when attempting to ascertain the relative contribution of these subtypes, in order to appropriately guide dry eye management. Although some clinical tests exist to assist with differentiating the sub-type of DED, such as the Schirmer test for aqueous deficiency and meibomian gland expression for evaporative dry eye, these procedures are generally invasive and their overall resolution is limited.

Although numerous diagnostic tests are routinely used, clinical diagnosis of DED remains complicated by considerable variability in its presentation and the weak association between traditional tests and patient symptoms. Most dry eye clinical diagnostic tests are poorly standardised, which confounds diagnostic accuracy in practice. There is also lack of universal consensus in relation to the optimal clinical diagnostic protocol for the condition. The International Dry Eye Workshop ("DEWS") Diagnostic Methodology Subcommittee in 2007 outlined an approach to diagnose DED: initial patient history, general ophthalmic examination, validated dry eye symptom questionnaire and at least two objective tests to assess tear film status, ocular surface health and/or meibomian gland integrity. However, DED diagnosis is clinically complex due to significantly variability in the self-reported diagnostic approaches for DED among clinicians in multiple demographics. Such inconsistency and inaccuracy in current approaches provides a need for improved diagnostic modalities for DED.

It would be desirable to provide novel diagnostic methods for reliably and accurately evaluating and monitoring DED in a subject, and which ameliorate and/or overcome one or more problems or inconveniences of certain of the prior art. It would also be desirable to provide novel diagnostic methods that are relatively simple, relatively rapid and objective, and which measure a single parameter to capture the complicated tear film physiological makeup and aetiology of DED for its identification in clinical settings. It would also be desirable to provide a computer program and device customised to perform the novel diagnostic methods.

A reference herein to a patent document or any other matter identified as prior art, is not to be taken as an admission that the document or other matter was known or that the information it contains was part of the common general knowledge as at the priority date of any of the claims.

SUMMARY

In one aspect, the present disclosure provides a method for evaluating Dry Eye Disease ("DED") in a human or animal subject, the method including the steps of: determining thread thinning dynamics of a tear sample of the subject using an acoustically-driven microfluidic extensional rheometry ("ADMiER") instrument; calculating at least one physical parameter value of the tear sample based at least in part on the determined thread thinning dynamics; and evaluating DED based at least in part on the calculated at least one physical parameter value of the tear sample.

The present disclosure provides a novel approach for assessing tear film integrity for clinical diagnosis and monitoring of DED, using acoustically-driven microfluidic extensional rheometry ("ADMiER") to quantify the viscoelastic properties of human or animal tears. Advantageously, DED can be evaluated based on calculation of a single physical parameter to capture the subject's tear film status. Furthermore, the calculation of the single physical parameter is relatively simple, relatively rapid and objective through use of the ADMiER instrument which reliably determines thread thinning dynamics of the tear sample. Further physical parameters may be used to provide additional information about the DED diagnosis.

In some embodiments, determining thread thinning dynamics includes the steps of obtaining thread thinning data of the tear sample using the ADMiER instrument and analysing the thread thinning data to determine the thread thinning dynamics. The thread thinning data may be obtained by forming a fluid capillary bridge of the tear sample using the ADMiER instrument and measuring changes in radius along the fluid capillary bridge during thread thinning. In certain embodiments, the radius of the fluid capillary bridge is measured at a neck, which is defined as the location where the thread first pinches and ruptures under capillary stresses. The ADMiER instrument may be provided with opposing plates between which a fluid capillary bridge can be formed, and an acoustic wave actuator having a working surface located on one of the plates. A fluid capillary bridge of the tear sample may be produced between the plates by applying the tear sample to the working surface of the acoustic wave actuator and energising the acoustic wave actuator. The acoustic wave actuator may be configured to use surface acoustic waves ("SAW"), bulk waves, surface reflected bulk waves ("SRBW"), or combinations thereof.

The thread thinning dynamics may be monitored using a detector and illuminator configured to capture images of the fluid capillary bridge during thread thinning. In some embodiments, the detector is a high-speed camera with microscopic lens attachment and the illuminator is facilitated with an LED, however various detection mechanisms may be used to monitor the change in the thread dimension, including, but not limited to, laser micrometers, line scan cameras, photodetectors or portable or mobile phone cameras with magnification lenses. The neck radius may be extracted from the images using standard image-analysis techniques. Alternatively, the ADMiER instrument may include a sensor configured to measure the changes in radius along the fluid capillary bridge during thread thinning. In certain embodiments, the sensor is a line scan camera that functions as an optical micrometer for relatively compact and robust measurement of the tear film capillary thinning.

In some embodiments, the method further includes the step of collecting a basal tear sample from an eye of the subject. The basal tear sample may be non-invasively collected from the subject's eye, such as with the use of a microcapillary tube. The collected tear sample may be dispensed into a sampling cartridge, which is loaded into a device housing the ADMiER instrument. The device enables automation of one or more of the method steps for relatively fast processing of the thread thinning dynamics and evaluation of DED. The tear sample may have a volume in a range of 1 nL to 10 mL, and such as a volume in a range of 1 to 2 µL.

The method may also include the step of identifying one or more reference values for evaluating DED. The one or more reference values may be identified from data obtained from a population of individuals. The data may be located in a database which is accessible by the clinician. The step of evaluating DED may include the steps of comparing the at least one physical parameter value with the one or more reference values and evaluating DED based on the comparison of the at least one physical parameter value with the one or more reference values.

In some embodiments, evaluating DED includes one or more of the following steps: diagnosing the presence of DED; assessing the severity of DED; and identifying a clinical sub-type of DED. The one or more reference values identified may include at least one threshold value or range of reference values indicative of one or more of the following: the presence of DED; the severity of DED; and a clinical sub-type of DED.

The presence of DED may be diagnosed when the at least one physical parameter value is less than a threshold value or within a range of reference values indicative of the presence of DED. The step of assessing the severity of DED may include the step of classifying the severity as borderline DED or definitive DED. The severity may be classified as borderline DED or definitive DED when the at least one physical parameter value is less than a respective threshold value or within a respective range of reference values indicative of borderline DED or definitive DED.

The step of assessing the severity of DED may further include classifying a clinical severity of definitive DED as one of mild, moderate or severe definitive DED. The clinical severity of definitive DED may be classified based at least in part on the at least one physical parameter value and a further physical parameter value of the tear sample.

The step of identifying a clinical sub-type of DED may include the step of classifying a clinical sub-type of DED as one or both of aqueous deficient DED and evaporative DED. The step of identifying a clinical sub-type of DED may further include the step of classifying a predominant clinical sub-type of DED as one of predominant aqueous deficient DED or predominant evaporative DED. The clinical sub-type may be classified as one or both of aqueous deficient DED and evaporative DED and one of predominant aqueous deficient DED or predominant evaporative DED when the at least one physical parameter value is less than a respective threshold value or within a respective range of reference values indicative of one or both of aqueous deficient DED and evaporative DED and one of predominant aqueous deficient DED or predominant evaporative DED.

In some embodiments, the method further includes providing one or more outcomes of the evaluation of DED. The method may further include the step of providing one or more outcomes of a previous evaluation of DED for the subject. The one or more outcomes may include one or more of the following: the presence of DED; borderline DED or definitive DED; mild, moderate or severe definitive DED; aqueous deficient DED and/or evaporative DED; and predominant aqueous deficient DED or predominant evaporative DED. The method may further include the step of monitoring DED by comparing the one or more outcomes of the evaluation of DED with the previous evaluation of DED and observing changes in the one or more outcomes. For example, the changes observed may be deviations or trends in the one or more outcomes.

The at least one physical parameter value may be selected from one of a group including: surface/interface tension; surface/interface viscosity; surface/interface elasticity; final break-up time; relaxation time; shear viscosity and extensional viscosity. In some embodiments, the at least one physical parameter value manifests as an apparent viscosity based on the extensional measurement obtained using the ADMiER instrument.

The range of reference values indicative of the presence of DED may include the range of about 0.0001 Pa·s to about 0.025 Pa·s, preferably about 0.0031 Pa·s to about 0.0151 Pa·s, and more preferably about 0.0059 Pa·s to about 0.0115 Pa·s. The range of reference values indicative of definitive DED may include the range of about 0.0031 Pa·s to about 0.0151 Pa·s, and preferably, about 0.0059 Pa·s to about 0.0079 Pa·s. Further, the range of reference values indicative of borderline DED may include the range of about 0.0002 Pa·s to about 0.03 Pa·s, preferably about 0.00455 Pa·s to about 0.0259 Pa·s and more preferably about 0.0079 Pa·s to about 0.0115 Pa·s. The threshold value indicative of the presence of DED may include about 0.0115 Pa·s, preferably, about 0.00873 Pa·s, and more preferably about 0.0093 Pa·s. The threshold value indicative of definitive DED may include about 0.0093 Pa·s, and preferably, about 0.0079 Pa·s. Definitive DED may be assessed when the measured tear extensional viscosity is less than the threshold values of about 0.0079 Pa·s or preferably about 0.0104 Pa·s otherwise, the severity of DED is assessed as borderline DED.

The range of reference values indicative of predominantly aqueous deficient DED may include the range of about 0.00307 Pa·s to about 0.0105 Pa·s. The range of reference values indicative of predominantly evaporative DED may include the range of about 0.00455 Pa·s to about 0.0151 Pa·s. Further, in a particular embodiment, of sensitivity approximately 63% and specificity approximately 62%, predominantly aqueous deficient DED may be classified when the measured tear extensional viscosity is less than threshold value of about 0.00651 Pa·s, otherwise evaporative DED is classified. The threshold value may vary depending on the sensitivity and specificity. The threshold values and range of references values indicative of predominantly aqueous deficient DED and predominantly evaporative DED may also be indicative of aqueous deficient DED and evaporative DED, respectively, for classification of the clinical sub-types of one or both of aqueous deficient DED and evaporative DED.

In another aspect, the present disclosure provides a device configured to evaluate Dry Eye Disease ("DED") in a human or animal subject, the device including: an acoustically-driven microfluidic extensional rheometry ("ADMiER") instrument; and a processing device configured to: determine thread thinning dynamics of a tear sample of the subject using the ADMiER instrument; calculate at least one physical parameter value of the tear sample based at least in part on the determined thread thinning dynamics; and evaluate DED based at least in part on the calculated at least one physical parameter value of the tear sample.

In some embodiments, the processing device is configured to determine thread thinning dynamics by receiving thread thinning data of the tear sample obtained using the ADMiER instrument and analysing the thread thinning data to determine the thread thinning dynamics. The thread thinning data may include changes in radius along a fluid capillary bridge of the tear sample during thread thinning. In certain embodiments, the changes in radius were measured at a neck of the fluid capillary bridge, which is defined as the location where the thread first pinches and ruptures under capillary stresses. The fluid capillary bridge may have been formed using the ADMiER instrument. The ADMiER instrument may include opposing plates between which a fluid capillary bridge can be formed, and an acoustic wave actuator having a working surface located on one of the plates. A fluid capillary bridge of the tear sample may be produced between the plates when the tear sample is applied to the working surface of the acoustic wave actuator and the acoustic wave actuator is energised. The acoustic wave actuator may be configured to use surface acoustic waves ("SAW"), bulk waves, surface reflected bulk waves ("SRBW") or combinations thereof.

The ADMiER instrument may also include a sensor configured to measure the changes in radius along the fluid capillary bridge during thread thinning to provide the thread thinning data. The device may include a memory device in communication with the processing device configured to store the thread thinning data. The ADMiER instrument may be in communication with the memory device for storage of the thread thinning data measured by the sensor. The memory device may also be in communication with the processing device so that the stored thread thinning data may be retrieved by the processing device for use in determining the thread thinning dynamics.

In some embodiments, the device includes a housing configured to receive a sampling cartridge storing the tear sample. The sampling cartridge may be housed separately from other components to preserve tear sample integrity. In some embodiments, the device may include an interface that separates the sampling cartridge from the ADMiER instrument and processing device. The device may be configured to dispense the tear sample from the sampling cartridge and apply it to the working surface of the acoustic wave actuator of the ADMiER instrument. Furthermore, the device may be configured to clean surfaces of the ADMiER instrument on receiving a new sampling cartridge. In certain embodiments, the sampling cartridge is disposable and for single-use. The tear sample volume may have a volume in a range of 1 nL to 10 mL, such as a volume in a range of 1 to 2 µL.

The processing device may be configured to receive one or more reference values for evaluating DED. The one or more reference values may be received from a memory device in communication with the processing device. The one or more reference values may have been identified using data obtained from a population of individuals. The processing device may also be configured to evaluate DED by comparing the at least one physical parameter value with the one or more reference values and evaluating DED based on the comparison of the at least one physical parameter value with the one or more reference values.

In some embodiments, the processing device is configured to evaluate DED by one or more of the following: diagnosing the presence of DED; assessing the severity of DED; and identifying a clinical sub-type of DED. The one or more reference values identified may include at least one threshold value or range of reference values indicative of one or more of the following: the presence of DED; the severity of DED; and a clinical sub-type of DED.

The processing device may be configured to evaluate DED by performing the steps of the method as described above for diagnosing the presence of DED, assessing the severity of DED and identifying a clinical sub-type of DED.

The processing device may be configured to diagnose the presence of DED when the at least one physical parameter value is less than a threshold value or within a range of reference values indicative of the presence of DED. The processing device may also be configured to assess the severity of DED by classifying the severity as borderline DED or definitive DED. The processing device may be configured to classify the severity as borderline DED or definitive DED when the at least one physical parameter value is less than a respective threshold value or within a respective range of reference values indicative of borderline DED or definitive DED.

In some embodiments, the processing device may be configured to assess the severity of DED by classifying a clinical severity of definitive DED as one of mild DED, moderate DED or severe DED. The clinical severity of definitive DED may be classified based at least in part on the at least one physical parameter value and a further physical parameter value of the tear sample. The processing device may be configured to receive the further physical parameter value of the tear sample from a memory device in communication with the processing device.

The processing device may be configured to identify a clinical sub-type of DED by classifying a clinical sub-type of DED as one or both of aqueous deficient DED and evaporative DED. The processing device may also be configured to identify a clinical sub-type of DED by further classifying a predominant clinical sub-type of DED as one of predominant aqueous deficient DED or predominant evaporative DED. The processing device may classify the clinical sub-type as one or both of aqueous deficient DED and evaporative DED and one of predominant aqueous deficient DED or predominant evaporative DED when the at least one physical parameter value is less than a respective threshold value or within a respective range of reference values indicative of one or both of aqueous deficient DED and evaporative DED and one of predominant aqueous deficient DED or predominant evaporative DED.

The processing device may also be configured to provide one or more outcomes of the evaluation of DED. The processing device may also be configured to provide one or more outcomes of a previous evaluation of DED for the subject. The one or more outcomes may include one or more of the following: the presence of DED; borderline DED or definitive DED; mild, moderate or severe definitive DED; aqueous deficient DED and/or evaporative DED; predominant aqueous deficient DED or predominant evaporative DED. The device may include a user interface configured to receive one or more outcomes of the previous evaluation of DED for the subject. The processing device may be configured to monitor DED in the subject by comparing the one or more outcomes of the evaluation of DED with the previous evaluation of DED and displaying changes in the one or more outcomes on a display device. For example, the changes may be deviations or trends in the one or more outcomes. This enables a clinician to identify changes in the subject's tear film status based on the deviations or trends in the at least one physical parameter value and outcomes of the evaluation of DED for long-term treatment and monitoring of DED.

The physical parameter value may be selected from one of a group including: surface/interface tension; surface/interface viscosity; surface/interface elasticity; final break-up time; relaxation time; shear viscosity and extensional viscosity. In some embodiments, the physical parameter value manifests as an apparent viscosity based on the extensional measurement obtained using the ADMiER instrument.

The range of reference values indicative of the presence of DED may include the range of about 0.0001 Pa·s to about 0.025 Pa·s, preferably about 0.0031 Pa·s to about 0.0151 Pa·s, and more preferably about 0.0059 Pa·s to about 0.0115 Pa·s. The range of reference values indicative of definitive DED may include the range of about 0.0031 Pa·s to about 0.0151 Pa·s, and preferably, about 0.0059 Pa·s to about 0.0079 Pa·s. Further, the range of reference values indicative of borderline DED may include the range of about 0.0002 Pa·s to about 0.03 Pa·s, preferably about 0.00455 Pa·s to about 0.0259 Pa·s and more preferably about 0.0079 Pa·s to about 0.0115 Pa·s. The threshold value indicative of the presence of DED may include about 0.0115 Pa·s, preferably, about 0.00873 Pa·s, and more preferably about 0.0093 Pa·s. The threshold value indicative of definitive DED may include about 0.0093 Pa·s, and preferably, about 0.0079 Pa·s. Definitive DED may be assessed when the measured tear extensional viscosity is less than the threshold values of about 0.0079 Pa·s or preferably about 0.0104 Pa·s otherwise, the severity of DED is assessed as borderline DED.

The range of reference values indicative of predominantly aqueous deficient DED may include the range of about 0.00307 Pa·s to about 0.0105 Pa·s. The range of reference values indicative of predominantly evaporative DED may include the range of about 0.00455 Pa·s to about 0.0151 Pa·s. Further, in a particular embodiment, of sensitivity approximately 63% and specificity approximately 62%, predominantly aqueous deficient DED may be classified when the measured tear extensional viscosity is less than threshold value of about 0.00651 Pa·s, otherwise evaporative DED is classified. The threshold value may vary depending on the sensitivity and specificity. The threshold values and range of references values indicative of predominantly aqueous deficient DED and predominantly evaporative DED may also be indicative of aqueous deficient DED and evaporative DED, respectively, for classification of the clinical sub-types of one or both of aqueous deficient DED and evaporative DED.

In another aspect, the present disclosure provides a method for evaluating Dry Eye Disease ("DED") in a human or animal subject, the method including the steps of: identifying one or more reference values for evaluating DED; identifying at least one physical parameter value of a tear sample of the subject, wherein the at least one physical parameter value has been calculated based at least in part on determined thread thinning dynamics of the tear sample; and evaluating DED based on a comparison of the identified at least one physical parameter value with the one or more reference values.

In some embodiments, evaluating DED includes one or more of the following steps: diagnosing the presence of DED; assessing the severity of DED; and identifying a clinical sub-type of DED. The one or more reference values identified may include at least one threshold value or range of reference values indicative of one or more of the following: the presence of DED; the severity of DED; and a clinical sub-type of DED. The step of evaluating DED may include the steps of the method as described above for diagnosing the presence of DED, assessing the severity of DED and identifying a clinical sub-type of DED.

The presence of DED may be diagnosed when the at least one physical parameter value is less than a threshold value or within a range of reference values indicative of the presence of DED. The step of assessing the severity of DED may include the step of classifying the severity as borderline DED or definitive DED. The severity may be classified as borderline DED or definitive DED when the at least one physical parameter value is less than a respective threshold value or within a respective range of reference values indicative of borderline DED or definitive DED.

The step of assessing the severity of DED may further include classifying a clinical severity of definitive DED as one of mild, moderate or severe definitive DED. The clinical severity of definitive DED may be classified based at least in part on the at least one physical parameter value and a further physical parameter value of the tear sample.

The step of identifying a clinical sub-type of DED may include the step of classifying a clinical sub-type of DED as one or both of aqueous deficient DED and evaporative DED. The step of identifying a clinical sub-type of DED may further include the step of classifying a predominant clinical sub-type of DED as one of predominant aqueous deficient DED or predominant evaporative DED. The clinical sub-type may be classified as one or both of aqueous deficient DED and evaporative DED and one of predominant aqueous deficient DED or predominant evaporative DED when the at least one physical parameter value is less than a respective threshold value or within a respective range of reference values indicative of one or both of aqueous deficient DED and evaporative DED and one of predominant aqueous deficient DED or predominant evaporative DED.

In some embodiments, the method further includes providing one or more outcomes of the evaluation of DED. The method may further include the step of providing one or more outcomes of a previous evaluation of DED for the subject. The one or more outcomes may include one or more of the following: the presence of DED; borderline DED or definitive DED; mild, moderate or severe definitive DED; aqueous deficient DED and/or evaporative DED; and predominant aqueous deficient DED or predominant evaporative DED. The method may further include the step of monitoring DED by comparing the one or more outcomes of the evaluation of DED with the previous evaluation of DED and observing changes in the one or more outcomes. For example, the changes observed may be deviations or trends in the one or more outcomes.

The physical parameter may be selected from one of a group including: surface/interface tension; surface/interface viscosity; surface/interface elasticity; final break-up time; relaxation time; shear viscosity and extensional viscosity. In some embodiments, the physical parameter value manifests as an apparent viscosity based on the extensional measurement obtained using the ADMiER instrument.

The range of reference values indicative of the presence of DED may include the range of about 0.0001 Pa·s to about 0.025 Pa·s, preferably about 0.0031 Pa·s to about 0.0151 Pa·s, and more preferably about 0.0059 Pa·s to about 0.0115 Pa·s. The range of reference values indicative of definitive DED may include the range of about 0.0031 Pa·s to about 0.0151 Pa·s, and preferably, about 0.0059 Pa·s to about 0.0079 Pa·s. Further, the range of reference values indicative of borderline DED may include the range of about 0.0002 Pa·s to about 0.03 Pa·s, preferably about 0.00455 Pa·s to about 0.0259 Pa·s and more preferably about 0.0079 Pa·s to about 0.0115 Pa·s. The threshold value indicative of the presence of DED may include about 0.0115 Pa·s, preferably, about 0.00873 Pa·s, and more preferably about 0.0093 Pa·s. The threshold value indicative of definitive DED may include about 0.0093 Pa·s, and preferably, about 0.0079 Pa·s. Definitive DED may be assessed when the measured tear extensional viscosity is less than the threshold values of about 0.0079 Pa·s or preferably about 0.0104 Pa·s otherwise, the severity of DED is assessed as borderline DED.

The range of reference values indicative of predominantly aqueous deficient DED may include the range of about 0.00307 Pa·s to about 0.0105 Pa·s. The range of reference values indicative of predominantly evaporative DED may include the range of about 0.00455 Pa·s to about 0.0151 Pa·s. Further, in a particular embodiment, of sensitivity approximately 63% and specificity approximately 62%, predominantly aqueous deficient DED may be classified when the measured tear extensional viscosity is less than threshold value of about 0.00651 Pa·s, otherwise evaporative DED is classified. The threshold value may vary depending on the sensitivity and specificity. The threshold values and range of references values indicative of predominantly aqueous deficient DED and predominantly evaporative DED may also be indicative of aqueous deficient DED and evaporative DED, respectively, for classification of the clinical sub-types of one or both of aqueous deficient DED and evaporative DED.

Additional features are described in, and will be apparent from the following Detailed Description and the figures.

BRIEF DESCRIPTION OF DRAWINGS

The disclosure will now be described in greater detail with reference to the accompanying drawings in which like features are represented by like numerals. It is to be understood that the embodiments shown are examples only and are not to be taken as limiting the scope of the disclosure as defined in the claims appended hereto.

DETAILED DESCRIPTION

Embodiments of the disclosure are discussed herein by reference to the drawings which are not to scale and are intended merely to assist with explanation of the disclosure. The inventive methods and device have utility in evaluating DED in human or animal subjects, particularly in one or more of diagnosing the presence of DED, assessing the severity as definitive DED or borderline DED and classifying a predominant clinical sub-type of DED as aqueous deficient DED or evaporative DED. Since DED is a highly prevalent condition, it is useful to provide accurate and reliable diagnostic methods and devices for evaluating DED.

Figure 1:
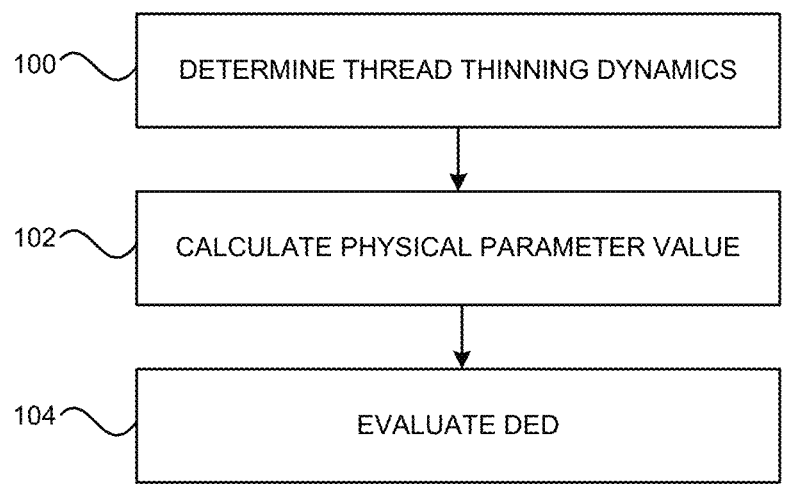
FIG. 1 is a flow chart illustrating the steps in a method for evaluating DED in a human or animal subject according to an embodiment of the disclosure.

FIG. 1 illustrates a flow chart showing steps in a method for evaluating DED in a human or animal subject according to certain embodiments of the disclosure. The method includes at step 100 determining thread thinning dynamics of a tear sample 228 of the subject using an acoustically-driven microfluidic extensional rheometry ("ADMiER") instrument 200 (see also FIG. 5). At least one physical parameter value of the tear sample 228 is calculated at step 102 based at least in part on the thread thinning dynamics determined at step 100. The method includes evaluating DED at step 104 based at least in part on the calculated at least one physical parameter value of the tear sample 228.

Figure 2:
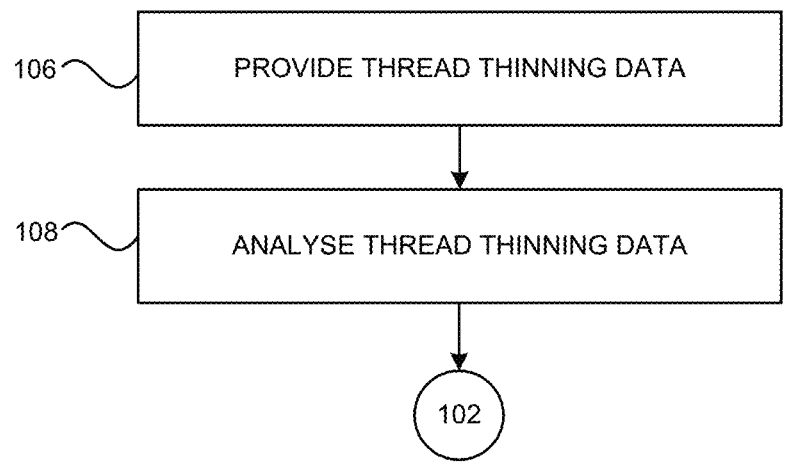
FIG. 2 is a flow chart illustrating further steps in the method of FIG. 1 relating to determining thread thinning dynamics according to an embodiment of the disclosure.

FIG. 2 illustrates a flow chart showing further steps in the method shown in FIG. 1. In some embodiments, determining thread thinning dynamics includes the step 106 of obtaining thread thinning data of the tear sample 228 using the ADMiER instrument 200. The method may also include further steps relating to obtaining thread thinning data as illustrated in the flow chart of FIG. 3. In some embodiments, the method includes at step 110 forming a fluid capillary bridge 224 of the tear sample 228 using the ADMiER instrument 200 (see also FIG. 5) and at step 112 measuring changes in radius along the fluid capillary bridge 224 during thread thinning to obtain the thread thinning data. The thread thinning data is then analysed at step 108 in FIG. 2 to determine thread thinning dynamics of the tear sample 228.

Figure 3:
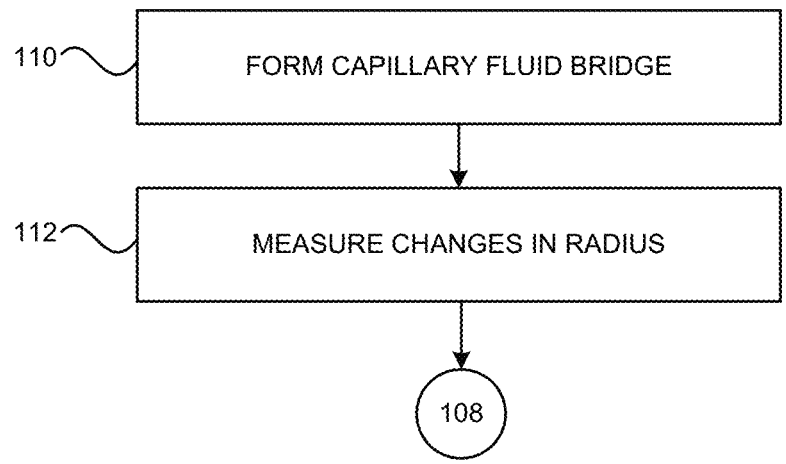
FIG. 3 is a flow chart illustrating further steps in the method of FIG. 2 relating to obtaining thread thinning data according to an embodiment of the disclosure.
Figure 4:
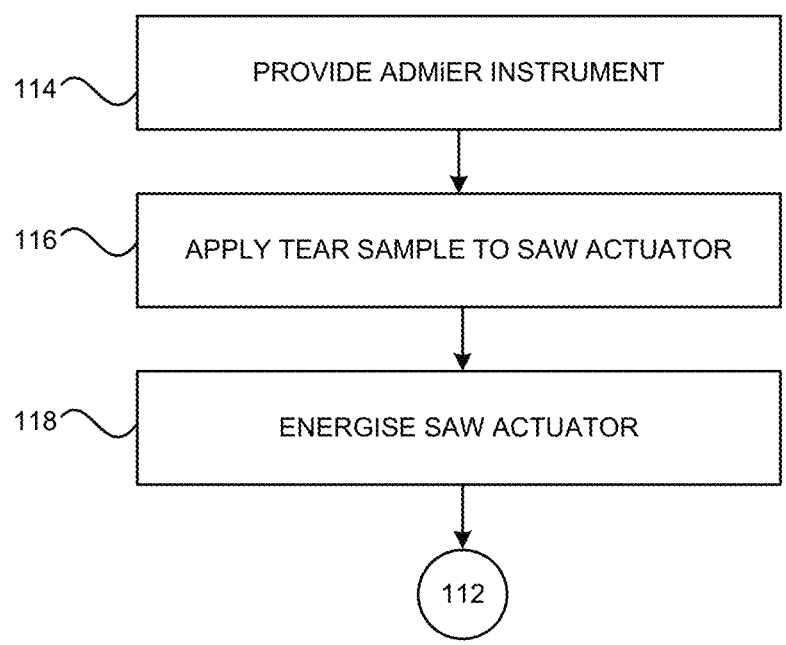
FIG. 4 is a flow chart illustrating further steps in the method of FIG. 3 relating to forming a fluid capillary bridge according to an embodiment of the disclosure.

FIG. 4 illustrates a flow chart showing further steps in the method of shown in FIG. 3 relating to forming the fluid capillary bridge 224. The method may include at step 114 providing the ADMiER instrument 200 with opposing plates 202, 204 between which a fluid capillary bridge 224 can be formed, and an acoustic wave actuator 206 having a working surface located on one of the plates 202 (see also FIG. 5). The method may include at step 116 applying the tear sample 228 to the working surface of the acoustic wave actuator 206 and at step 118 energising the acoustic wave actuator 206 to produce a fluid capillary bridge 224 of the tear sample 228 between the plates 202, 204.

Figure 5:
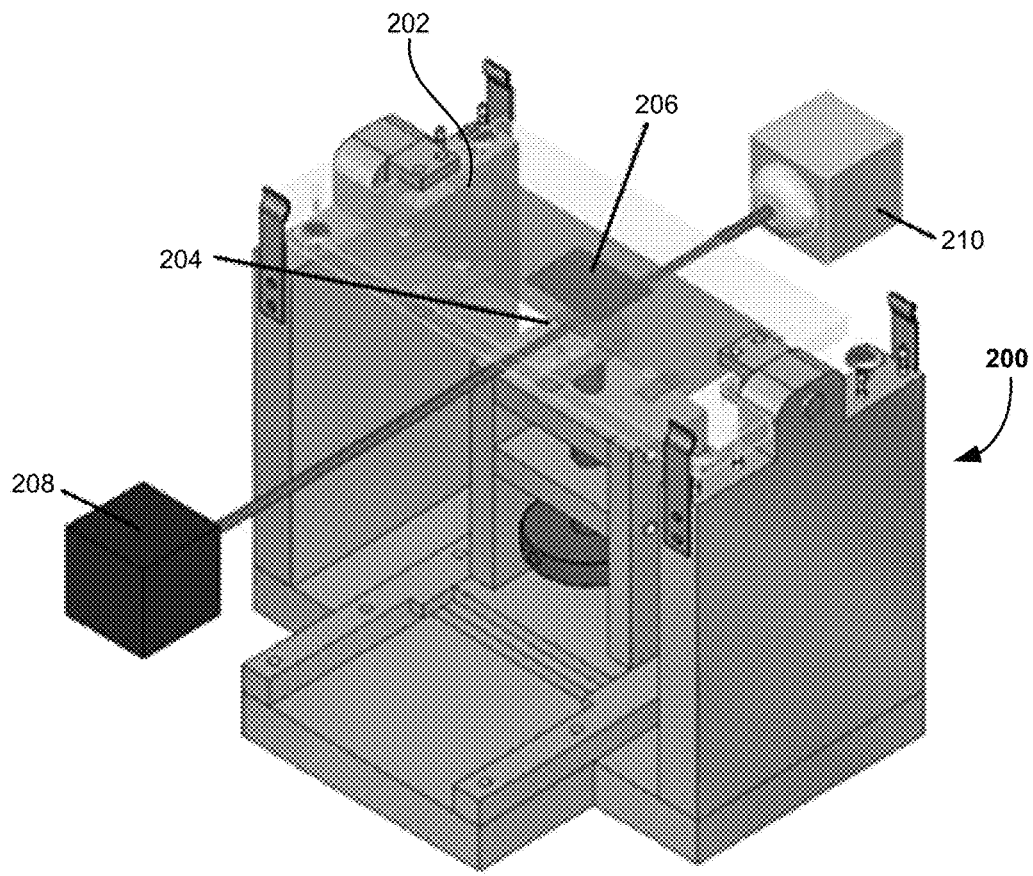
FIG. 5 shows an ADMiER instrument for use in the method of FIGS. 1 to 4 according to an embodiment of the disclosure.
Figure 6:
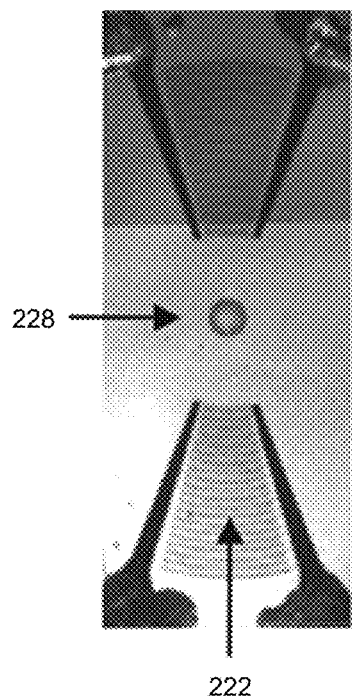
FIG. 6 is a plan view of the ADMiER instrument of FIG. 5 illustrating a tear droplet applied to one of the plates according to an embodiment of the disclosure.

An exemplary ADMiER instrument 200 is shown in FIGS. 5 and 6. The ADMiER instrument 200 includes an upper plate 202 having the acoustic wave actuator 206 and a lower plate 204. The acoustic wave actuator 206 may be configured to use surface acoustic waves ("SAW"), bulk waves, surface reflected bulk waves ("SRBW"), or combinations thereof. In some embodiments, the acoustic wave actuator 206 is configured to generate a short ultrasonic pulse in the form of a surface acoustic wave ("SAW"). The acoustic wave actuator 206 may include a piezoelectric chip configured to generate SAWs by applying a pulsed AC signal to interdigital ("IDT") electrodes 222 on the chip at a frequency commensurate with the resonant frequency of the IDT as shown in FIG. 6. The pulsed signal parameter, IDT design and the thickness of the chip enable for the generation of a bulk, surface or a combined surface or bulk acoustic wave at the same frequency or at a higher harmonic frequency, such as 1 MHz to 100 GHz, that is launched on or through the chip with an amplitude that ranges from between 1 picometre (pm) to 100 nanometres (nm), although the amplitude to generate the fluid capillary bridge from a microliter drop is typically around 10 nm. In certain embodiments, the SAW generated has an amplitude of approximately 10 nm.

Figure 7:
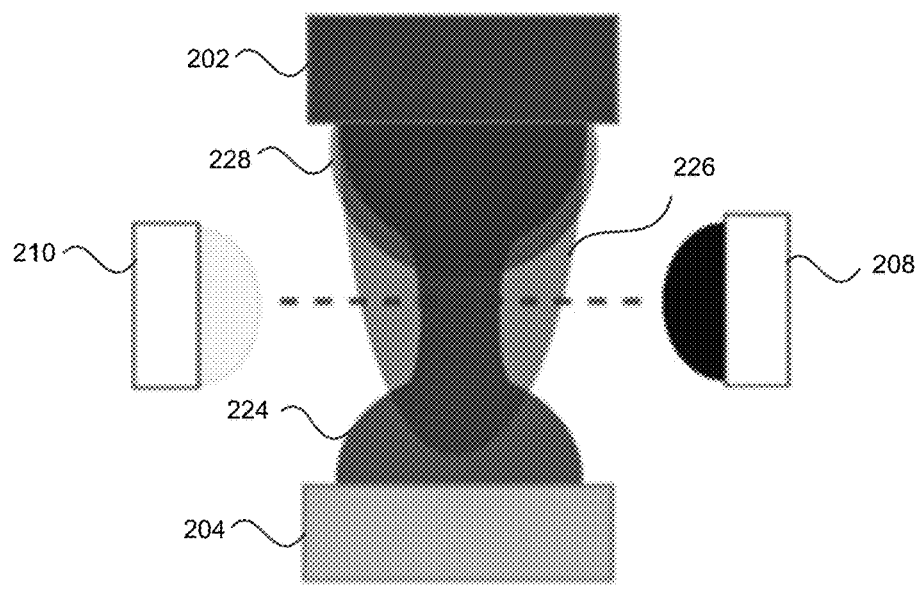
FIG. 7 is a schematic illustrating formation of a fluid capillary bridge according to an embodiment of the disclosure.

The working surface of the acoustic wave actuator 206 having the piezoelectric chip may be located on an underside of the upper plate 202. As shown in FIGS. 6 and 7, the tear sample 228 is applied to the working surface in the form of a sessile droplet 228. The droplet may have a diameter of approximately 1 mm. The acoustic wave actuator 206 then generates a SAW burst 226 to jet the sessile droplet 228 toward the lower plate 204. This results in formation of a fluid capillary bridge 224 between the upper and lower plates 202, 204. In alternative embodiments, the acoustic wave actuator 206 having the piezoelectric chip may be located on a topside of the lower plate 204 (not shown). When the SAW burst 226 is generated by the acoustic wave actuator 206, the sessile droplet 228 is jetted from the topside of the lower plate 204 to the upper plate 204 against gravity to form the fluid capillary bridge 224. In both embodiments, the fluid capillary bridge 224 subsequently thins under capillary stresses and ruptures below a critical thread thickness due to the fluid's surface tension and resisted by its viscosity.

Figure 8:
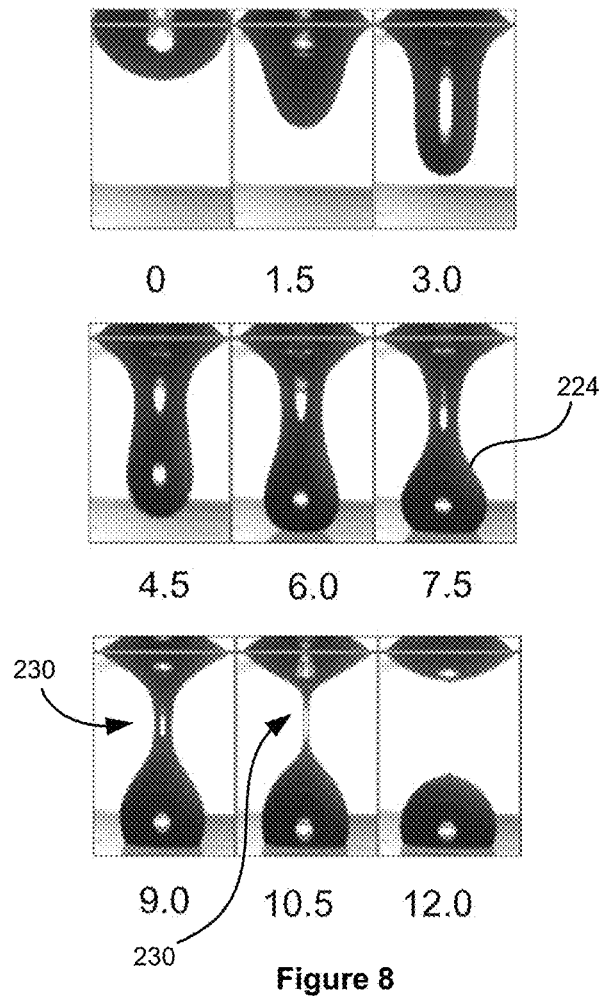
FIG. 8 shows a series of time lapse photos illustrating formation of a fluid capillary bridge and thinning under capillary stresses according to an embodiment of the disclosure.

FIG. 8 shows a series of milli-second time lapse photos illustrating formation of the fluid capillary bridge 224 and thinning under capillary stresses. The sessile droplet 228 is applied to the working surface on the upper plate 202 initially and jetted toward the lower plate 204 from 1.5 to 6.0 ms. The fluid capillary bridge 224 is formed at 7.5 ms and then thins under capillary stresses from 9.0 to 10.5 ms. Finally, the fluid capillary bridge 224 ruptures below a critical thread thickness at 12.0 ms. The capillary thinning of the fluid capillary bridge 224 formed using the ADMiER instrument 200 follows established physics in its macroscopic counterpart—the Capillary Breakup Elongational Rheometer ("CaBER"). The CaBER is the subject of U.S. patent application Ser. No. 13/805,711, which is incorporated herein by this reference.

The thread thinning dynamics may be monitored using a detector 208 and illuminator 210 configured to capture images of the fluid capillary bridge 224 during thread thinning as shown in FIG. 8. The detector 208 may include a high-speed camera (e.g., Photron SA5) with a microscopic lens attachment (e.g., Infinity K2/SC) and the illuminator 210 may include an LED. The radius along the fluid capillary bridge 224 may be measured during thread thinning by extracting the radius in each image frame using standard image-analysis techniques. Alternatively, in some embodiments the ADMiER instrument 200 includes a sensor 310 (see also FIG. 15) configured to measure changes in radius along the fluid capillary bridge 224 during thread thinning. The sensor may be a line scan camera that functions as an optical micrometer to obtain thread thinning data of the changes in radius. In certain embodiments, the radius of the fluid capillary bridge 224 is measured at a neck 230 as shown in FIG. 8 from 9.0 to 10.5 ms. The neck 230 is defined as the location where the thread of the fluid capillary bridge 224 first pinches and ruptures under capillary stresses.

The thread thinning dynamics are governed by the filament and liquid properties, particularly its extensional viscosity and surface tension. This facilitates characterisation of complex physiological fluids, such as tear film samples, through viscoelastic properties derived using the ADMiER instrument 200. Such characterisation of physiological fluids however poses a considerable challenge for conventional extensional rheometers, particularly because of the difficulty in consistently generating capillary bridges for low viscosity fluids. Further, standard rheological analyses require large (i.e. millilitre) sample volumes, which are not feasible for tear samples. In contrast, the ADMiER instrument's 200 ability to form capillary bridges from microlitre samples of fluids with viscosities as low as that of water provide a unique platform for testing the viscoelastic properties of tear samples. Such small sample sizes and fast (e.g., less than 1 second) processing times are not only advantageous for diagnosis but also render evaporative and gravitational effects that typically confound the measurements negligible.

Figure 9:
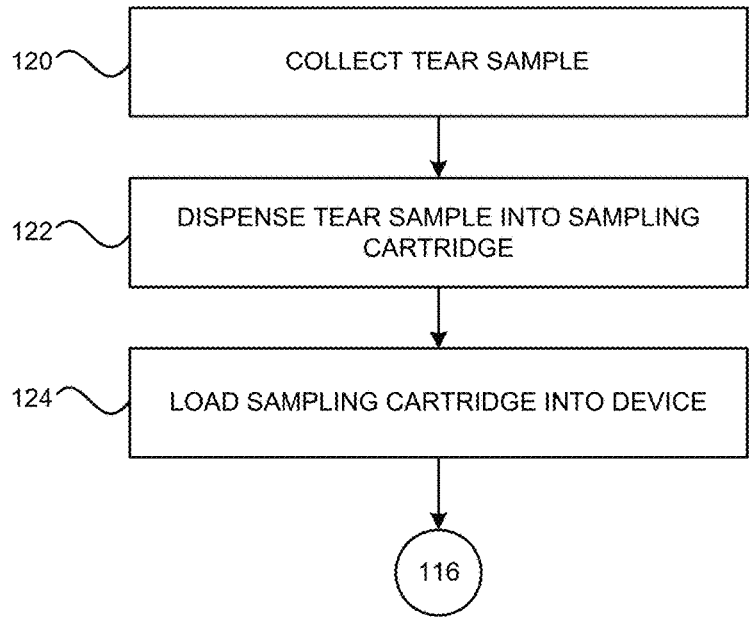
FIG. 9 is a flow chart illustrating further steps in the method of FIGS. 1 to 4 relating to collecting a tear sample according to an embodiment of the disclosure.

FIG. 9 is a flow chart illustrating further steps in the method of FIGS. 1 to 4 relating to collecting a tear sample according to an embodiment of the disclosure. The method includes at step 120 collecting a basal tear sample 228 from the subject's eye. The basal tear sample 228 may be non-invasively collected from the subject's eye, such as with the use of a microcapillary tube. In some embodiments, the method also includes the step 122 of dispensing the collected tear sample 228 into a sampling cartridge 318 (see also FIG. 15). The sampling cartridge 318 may be loaded into a device 300 housing the ADMiER instrument 200 (see also FIG. 15). The device 300 may enable automation of one or more of the method steps for relatively fast processing of the thread thinning dynamics and evaluation of DED. The tear sample 228 that is collected may have a volume in a range of 1 nL to 10 mL, such as a volume in a range of 1 to 2 µL.

Figure 10:
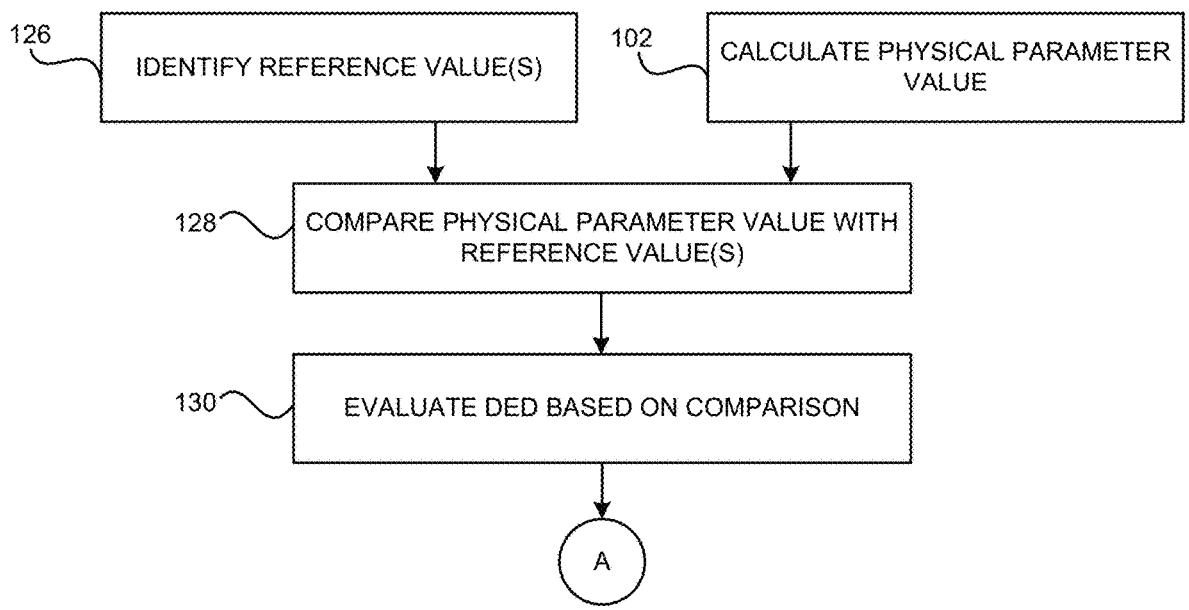
FIG. 10 is a flow chart illustrating further steps in the method of FIGS. 1 to 4 and 9 relating to evaluating DED according to an embodiment of the disclosure.

The method may also include further steps relating to evaluating DED as illustrated in the flow chart of FIG. 10. In step 126, one or more reference values are identified for evaluating DED. The reference values may be identified from data obtained from a population of individuals. The method may also include at step 128 comparing at least one physical parameter value calculated at step 102 with the identified reference values from step 126. DED is then evaluated at step 130 based on the comparison of the calculated at least one physical parameter value with the identified reference values.

Figure 11:
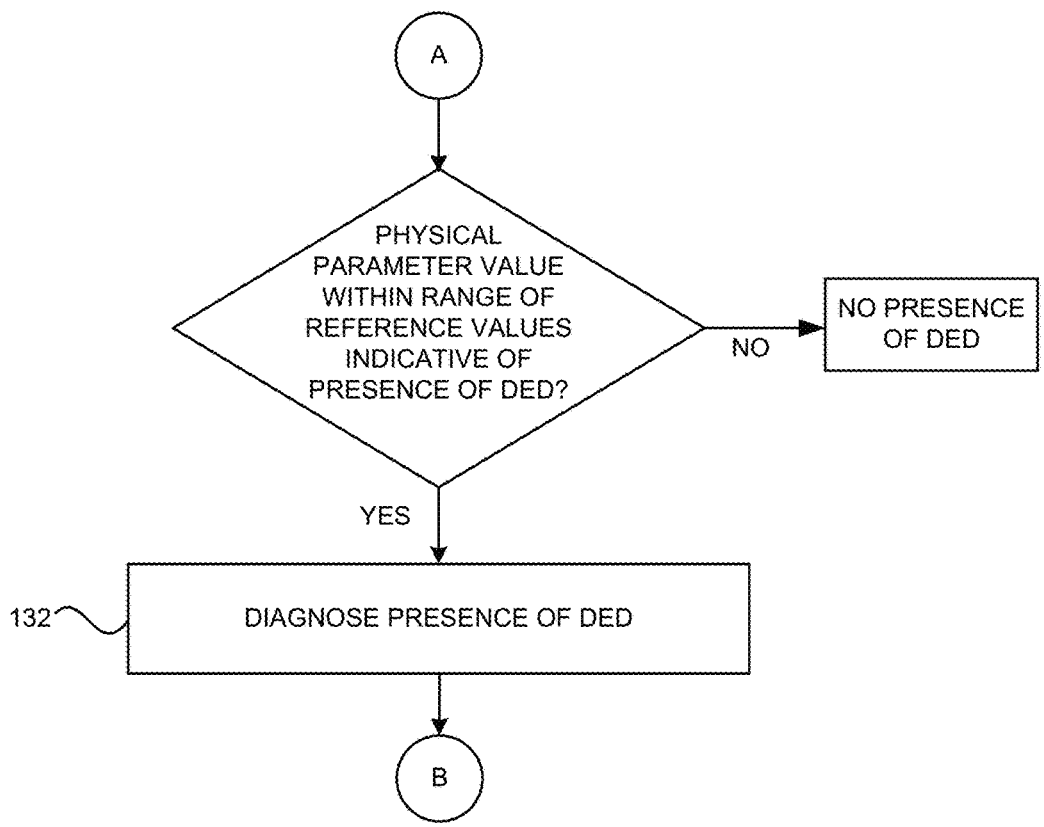
FIGS. 11 to 13 are flow charts illustrating further steps in the method of FIG. 10 relating to diagnosing the presence of DED, classifying the severity of DED as definitive DED or borderline DED, and classifying a predominant clinical sub-type of DED as evaporative DED or aqueous deficient DED according to embodiments of the disclosure.
Figure 12:
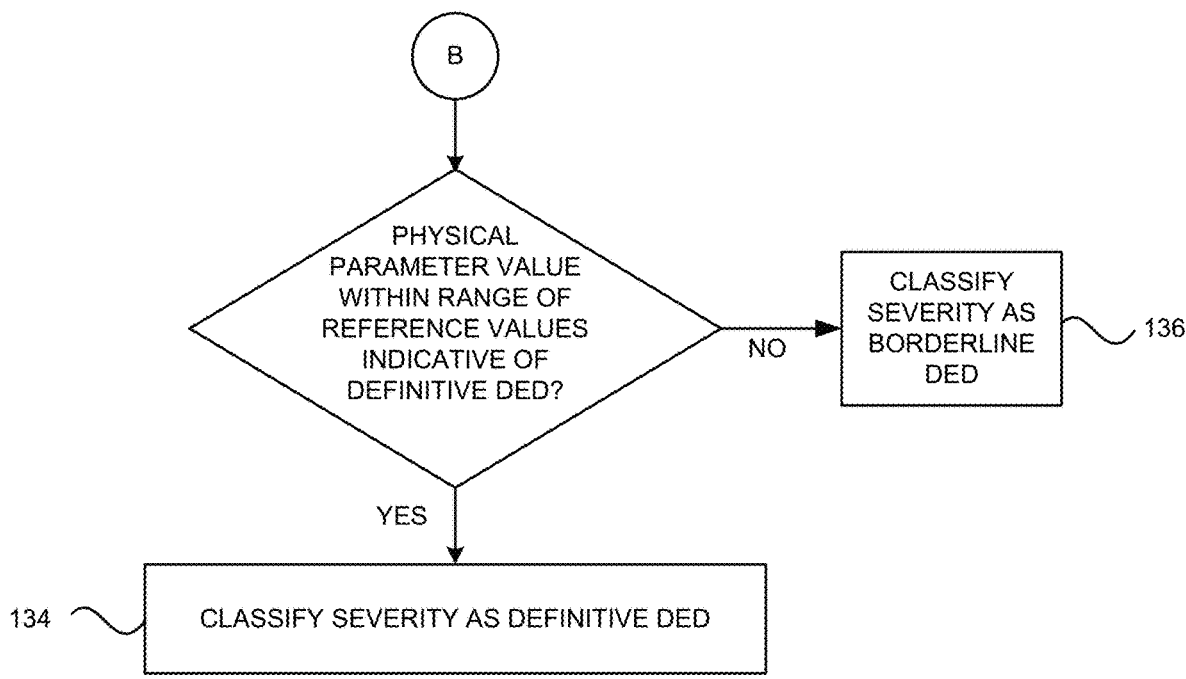
Figure 13:
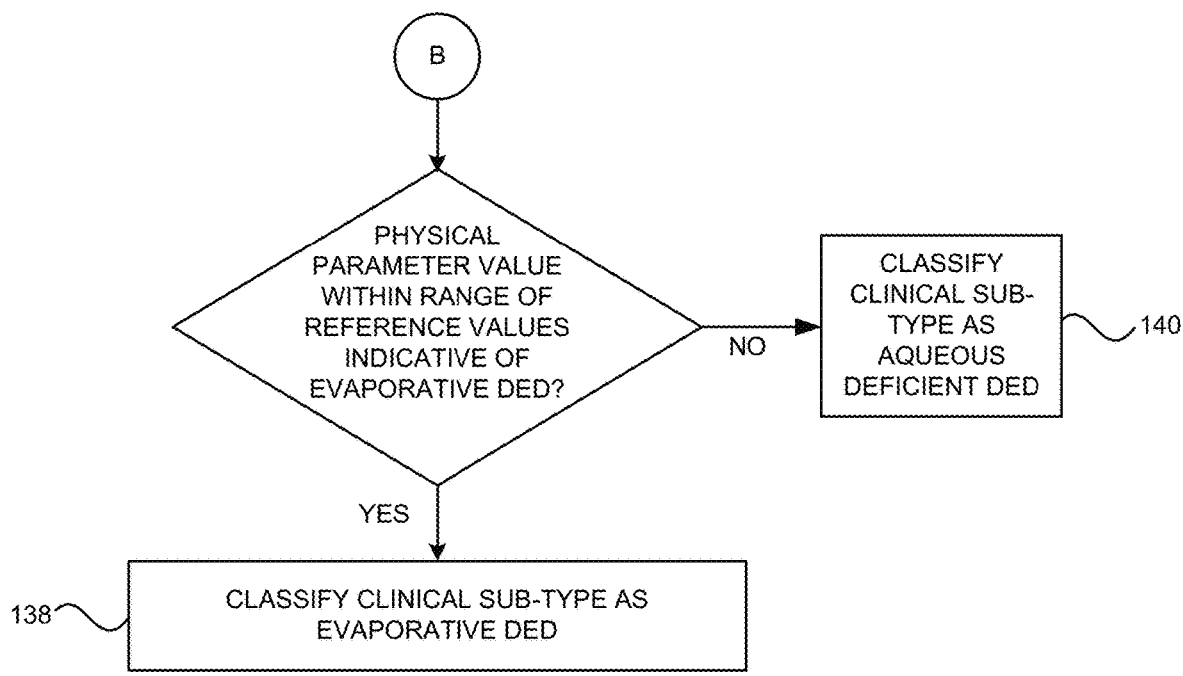

FIGS. 11 to 13 are flow charts illustrating further steps in the method of FIG. 10 relating to diagnosing the presence of DED at step 132, classifying the severity of DED as definitive DED or borderline DED at steps 134, 136, and classifying a predominant clinical sub-type of DED as aqueous deficient DED or evaporative DED at steps 138, 140. Each of the diagnostic methods involves a comparison of the physical parameter values with a respective threshold value or range of reference values indicative of the particular evaluation of DED. Accordingly, the identified reference values may include at least one threshold value or range of reference values indicative of one or more of the following: the presence of DED, the severity of DED and a clinical sub-type of DED.

FIG. 11 shows that the presence of DED is diagnosed at step 132 when the at least one physical parameter value is less than a threshold value or within a range of reference values indicative of the presence of DED. Otherwise, there is no presence of DED in the subject (i.e., the subject has a healthy tear film). Once the presence of DED has been diagnosed, the severity and predominant clinical sub-type may be classified by the steps of the flow charts in FIGS. 12 and 13. FIG. 12 shows that assessing the severity of DED includes classifying the severity as definitive DED at step 134 or borderline DED at step 136. The severity is classified as definitive DED at step 134 when the at least one physical parameter value is less than a threshold value or within a range of reference values indicative of definitive DED. Otherwise, the severity is classified as borderline DED at step 136.

Although not shown, the method may include identifying a clinical sub-type of DED by classifying a clinical sub-type of DED as one or both of aqueous deficient DED and evaporative DED. Accordingly, the subject may exhibit the following types of DED: (i) aqueous deficient DED only; (ii) evaporative DED only; or both aqueous deficient and evaporative DED. Advantageously, the present disclosure may enable the presence of each of these clinical sub-types of DED to be identified. The clinical sub-type is classified as one or both of aqueous deficient DED and evaporative DED when the at least one physical parameter value is less than a threshold value or within a range of reference values indicative of aqueous deficient DED and/or evaporative DED.

FIG. 13 shows that identifying a clinical sub-type of DED may include classifying a predominant clinical sub-type as predominant aqueous deficient DED at step 138 or predominant evaporative DED at step 140. The clinical sub-type is classified as predominant aqueous deficient DED at step 138 when the at least one physical parameter value is less than a threshold value or within a range of reference values indicative of predominant aqueous deficient DED. Otherwise, the clinical sub-type is classified as predominant evaporative DED at step 140.

In some embodiments (not shown), assessing the severity of DED further includes classifying a clinical severity of definitive DED as one of mild, moderate or severe definitive DED. The clinical severity of definitive DED may be classified based at least in part on the at least one physical parameter value and a further physical parameter value of the tear sample.

In some embodiments (not shown), the method further includes providing one or more outcomes of the evaluation of DED. The method may further include the step of providing one or more outcomes of a previous evaluation of DED for the subject. The one or more outcomes may include one or more of the following: the presence of DED; borderline DED or definitive DED; mild, moderate or severe definitive DED; aqueous deficient DED and/or evaporative DED; and predominant aqueous deficient DED or predominant evaporative DED. The method may further include the step of monitoring DED by comparing the one or more outcomes of the evaluation of DED with the previous evaluation of DED and observing changes in the one or more outcomes. For example, the changes observed may be deviations or trends in the one or more outcomes.

Accordingly, embodiments of the disclosure advantageously provide for evaluation of DED in the subject and the ability to differentiate between healthy subjects, and those subjects with borderline DED or definitive DED. Further, for those subjects evaluated to have definitive DED, embodiments of the disclosure also advantageously provide for evaluation of the severity of definitive DED, as one of mild, moderate and severe definitive DED. The ability to stratify based upon disease severity for DED is desirable for evaluating and monitoring DED.

Figure 14:
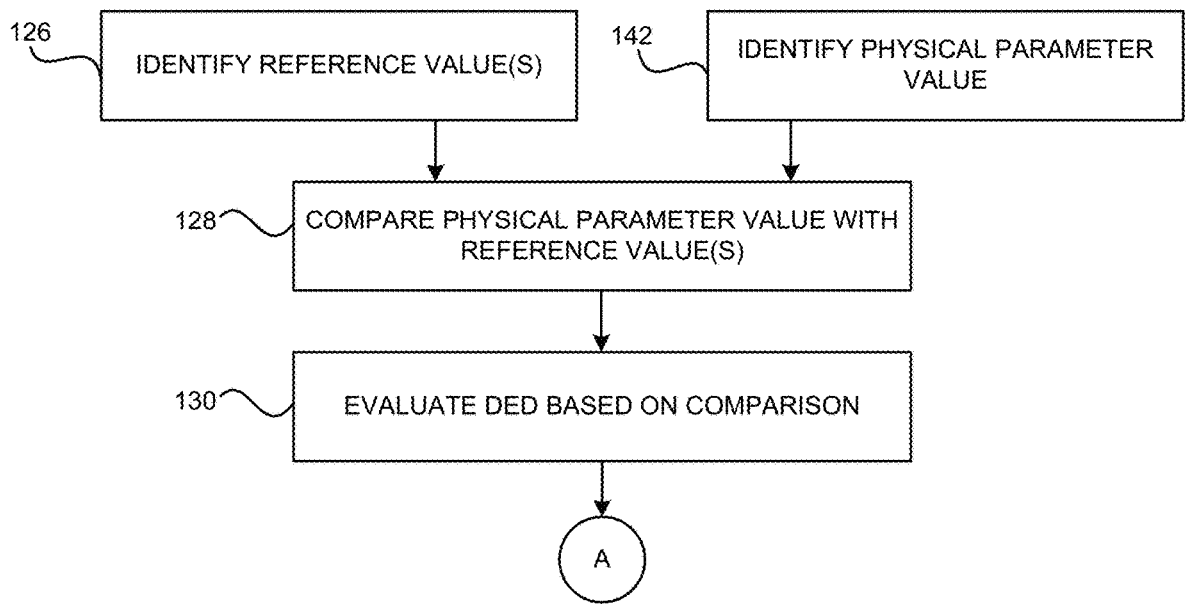
FIG. 14 is a flow chart illustrating the steps in another method for evaluating DED in a human or animal subject according to an embodiment of the disclosure.

FIG. 14 illustrates a flow chart showing steps in another method for evaluating DED in a human or animal subject according to certain embodiments of the disclosure. The method includes at step 126 identifying one or more reference values for evaluating DED. The method also includes at step 142 identifying at least one physical parameter value of a tear sample 228 of the subject. The at least one physical parameter value has been calculated based at least in part on determined thread thinning dynamics of the tear sample 228. In some embodiments, the effect of the at least one physical parameter value is calculated as an apparent viscosity based at least in part on determined extensional measurement of the thread thinning dynamics of the tear sample 228. The method also includes at steps 128 and 130 evaluating DED based on a comparison of the identified at least one physical parameter value with the one or more reference values.

In some embodiments, the method includes diagnosing the presence of DED at step 132, classifying the severity of DED as definitive DED or borderline DED at steps 134, 136, and identifying a clinical sub-type of DED by classifying a predominant clinical sub-type of DED as predominant aqueous deficient DED or predominant evaporative DED at steps 138, 140 by performing the steps shown in FIGS. 11 to 13. Accordingly, the identified one or more reference values may include at least one threshold value or range of reference values indicative of one or more of the following: the presence of DED, the severity of DED and a clinical sub-type of DED. Furthermore, the thread thinning dynamics may be determined using the ADMiER instrument 200 according to any one of the steps of the method as described herein and particularly with reference to FIGS. 2 to 4.

Figure 15:
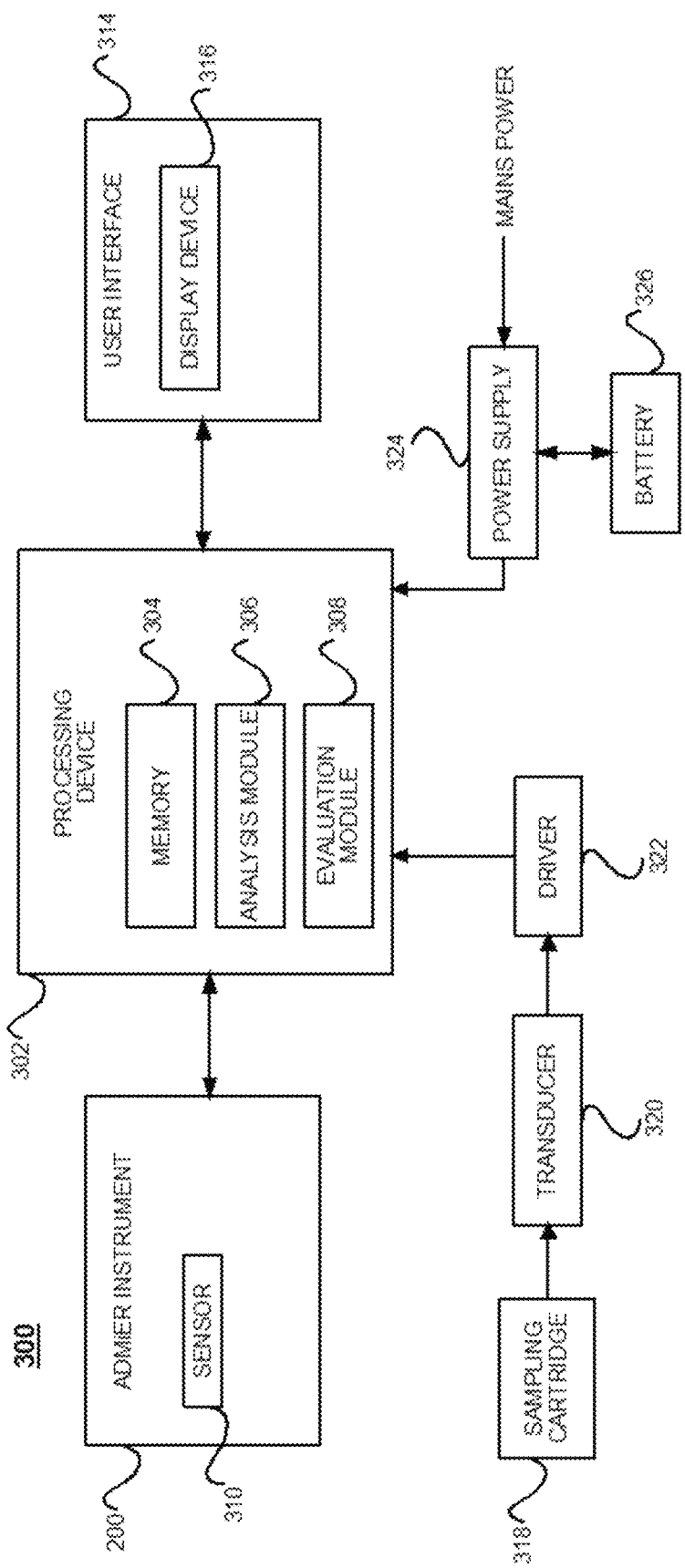
FIG. 15 is a schematic illustration showing components of a device for evaluating DED in a human or animal subject according to an embodiment of the disclosure.

In one embodiment of the disclosure, a computer program product is provided that stores instructions configured to control a processing device 302 to evaluate DED in a human or animal subject (see also FIG. 15). The processing device 302 may include a processor or a controller as would be appreciated by a person skilled in the art. The instructions may cause the processing device 302 to determine thread thinning dynamics of a tear sample 228 of the subject using an ADMiER instrument 200 and calculate at least one physical parameter value of the tear sample 228 based at least in part on the determined thread thinning dynamics. The instructions may also cause the processing device to evaluate DED based at least in part on the calculated at least one physical parameter value of the tear sample 228.

The instructions may cause the processing device 302 to receive thread thinning data of the tear sample 228 obtained using the ADMiER instrument 200 and analyse the thread thinning data to determine the thread thinning dynamics. The thread thinning data may include changes in radius along a fluid capillary bridge 224 of the tear sample 228 during thread thinning. The fluid capillary bridge 224 may have been formed using the ADMiER instrument 200 as described herein. The instructions may cause the processing device 302 to determine the thread thinning dynamics using the ADMiER instrument 200 according to any one of the steps of the methods as described herein and particularly with reference to FIGS. 2 to 4.

In some embodiments, the thread thinning data is received from a memory device 304 in communication with the processing device 302 (see also FIG. 15). The instructions may also cause the processing device 302 to receive one or more reference values for evaluating DED. The reference values may be received from the memory device 304 and may have been identified using data obtained from a population of individuals. The instructions may further cause the processing device 302 to evaluate DED by comparing the at least one physical parameter value with the one or more reference values and evaluating DED based on the comparison.

The instructions may also cause the processing device 302 to evaluate DED by diagnosing the presence of DED at step 132, classifying the severity of DED as definitive DED or borderline DED at steps 134, 136, and identifying a clinical sub-type of DED by classifying a predominant clinical sub-type of DED as predominant aqueous deficient DED or predominant evaporative DED at steps 138, 140 by performing the steps of the method shown in FIGS. 11 to 13. The instructions may also cause the processing device 302 to identify a clinical sub-type of DED by classifying a clinical sub-type of DED as one or both of aqueous deficient DED and evaporative DED (not shown). Accordingly, the identified one or more reference values may include at least one threshold value or range of reference values indicative of one or more of the following: the presence of DED, the severity of DED and a clinical sub-type of DED.

In some embodiments, the instructions cause the processing device to generate a display signal configured to cause a display device 316 to provide one or more outcomes of the evaluation of DED (see also FIG. 15). The one or more outcomes may include one or more of the following: the presence of DED; borderline or definitive DED; aqueous deficient DED and/or evaporative DED; and predominant aqueous deficient DED or predominant evaporative DED. The instructions may also cause the processing device 302 to receive one or more outcomes of a previous evaluation of DED, such as from the memory device 304. In some embodiments, the instructions cause the processing device 302 to compare the one or more outcomes of the evaluation of DED with the previous evaluation of DED and display trends or deviations in the one or more outcomes on the display device 316.

In one embodiment of the disclosure, another computer program product is provided that stores instructions configured to control a processing device 302 to evaluate DED in a human or animal subject (see also FIG. 15). The instructions may cause the processing device 302 to receive one or more reference values for evaluating DED, identify at least one physical parameter value of a tear sample 228 of the subject and evaluate DED based on a comparison of the identified at least one physical parameter value with the one or more reference values. The at least one physical parameter value may have been calculated based at least in part on determined thread thinning dynamics of the tear sample 228. In some embodiments, the effect of the at least one physical parameter value is calculated as an apparent viscosity based at least in part on determined extensional measurement of the thread thinning dynamics of the tear sample 228.

The instructions may cause the processing device 302 to evaluate DED by diagnosing the presence of DED at step 132, classifying the severity of DED as definitive DED or borderline DED at steps 134,136, and identifying a clinical sub-type of DED by classifying a predominant clinical sub-type of DED as predominant aqueous deficient DED or predominant evaporative DED at steps 138, 140 by performing the steps of the method shown in FIGS. 11 to 13. The instructions may also cause the processing device 302 to identify a clinical sub-type of DED by classifying a clinical sub-type of DED as one or both of aqueous deficient DED and evaporative DED (not shown). Accordingly, the identified one or more reference values may include at least one threshold value or range of reference values indicative of one or more of the following: the presence of DED, the severity of DED and a clinical sub-type of DED.

FIG. 15 is a schematic illustration showing components of a device 300 for evaluating DED in a human or animal subject according to certain embodiments of the disclosure. The device 300 includes an ADMiER instrument 200 and a processing device 302. The processing device 302 is configured to: determine thread thinning dynamics of a tear sample 228 of the subject using the ADMiER instrument 200; calculate at least one physical parameter value of the tear sample 228 based at least in part on the determined thread thinning dynamics; and evaluate DED based at least in part on the calculated at least one physical parameter value of the tear sample 228.

In some embodiments, the processing device 302 includes an analysis module 306 configured to determine thread thinning dynamics. The analysis module 306 determines thread thinning dynamics by receiving thread thinning data of the tear sample 228 obtained using the ADMiER instrument 200 and analysing the thread thinning data to determine the thread thinning dynamics. The thread thinning data may include changes in radius along a fluid capillary bridge 224 of the tear sample 228 during thread thinning. The fluid capillary bridge 224 may have been formed using the ADMiER instrument 200 as described herein and particularly with reference to FIGS. 2 to 8. The device 300 may also include a memory device 304 in communication with the processing device 302 configured to store the thread thinning data. The analysis module 306 is also configured to calculate the at least one physical parameter value of the tear sample 228 based at least in part on the determined thread thinning dynamics. In some embodiments, the effect of the at least one physical parameter value is calculated as an apparent viscosity based at least in part on determined extensional measurement of the thread thinning dynamics of the tear sample 228. The calculation may be performed using established methods as described in U.S. patent application Ser. No. 13/805,711, which is incorporated herein by this reference.

The processing device 302 may also include an evaluation module 308 configured to evaluate DED. The evaluation module 308 may be configured to receive one or more reference values for evaluating DED, such as from the memory device 304. The one or more reference values may have been identified using data obtained from a population of individuals. The evaluation module 308 may also be configured to evaluate DED by comparing the at least one physical parameter value with the one or more reference values and evaluating DED based on the comparison.

The evaluation module 308 may be configured to evaluate DED by one or more of the following: diagnosing the presence of DED; assessing the severity of DED and identifying a clinical sub-type of DED. In some embodiments, the evaluation module 308 is configured to perform steps of one or more of the methods shown in FIGS. 11 to 13, such as diagnosing the presence of DED at step 132, classifying the severity of DED as definitive DED or borderline DED at steps 134, 136, and identifying a clinical sub-type of DED by classifying a predominant clinical sub-type of DED as aqueous deficient DED or evaporative DED at steps 138, 140. The evaluation module 308 may also be configured to identify a clinical sub-type of DED by classifying a clinical sub-type of DED as one or both of aqueous deficient DED and evaporative DED (not shown). Accordingly, the identified one or more reference values may include at least one threshold value or range of reference values indicative of one or more of the following: the presence of DED, the severity of DED and a clinical sub-type of DED.

In some embodiments, the processing device 302 is configured to display on a display device 316 one or more outcomes of the evaluation of DED. The display device 316 may be included in the device 300 as shown in FIG. 15. The one or more outcomes may include one or more of the following: the presence of DED; borderline or definitive DED; aqueous deficient DED and/or evaporative DED; and predominant aqueous deficient DED or predominant evaporative DED. The device 300 may also include a user interface 314 as shown in FIG. 15. The user interface 314 may be configured to receive one or more outcomes of a previous evaluation of DED, such as from the memory device 304. The evaluation module 308 may be configured to compare the one or more outcomes of the evaluation with the previous evaluation of DED and display trends or deviations in the one or more outcomes on the display device 316.

The device 300 may include a housing configured to receive a sampling cartridge 318 storing the tear sample 228 (not shown). The device 300 may house the ADMiER instrument 200, processing device 302, user interface 314 with display device 316 along with the sampling cartridge 318 as an integrated assembly. In certain embodiments, the sampling cartridge 318 is housed separately from other components in the device 300 to preserve tear sample integrity. The device 300 may also include a transducer 320 and driver 322 configured to detect loading and unloading of the sampling cartridge 318 from the device housing as shown in FIG. 15.

In some embodiments, the device 300 may be configured to dispense the tear sample 228 from the sampling cartridge 318 and apply it to the working surface of the acoustic wave actuator 206 of the ADMiER instrument 200. Additionally, the device 300 may be configured to clean surfaces of the ADMiER instrument on receiving a new sampling cartridge 318. The device 300 may clean one or more of the working surface of the acoustic wave actuator 206, the plate 202 of the ADMiER instrument 200 and the plate 204 of the ADMiER instrument 200. In certain embodiments, the device 300 cleans the working surface and plates 202, 204 of the ADMiER instrument 200. In some embodiments, the sampling cartridge may be disposable and for single use.

As shown in FIG. 15, the device 300 may include a power supply 324 connected to mains power and a battery 326 connected to the power supply 324. The battery 326 may be rechargeable for portable use of the device 300, such as in hospitals or clinics, or in pathology testing facilities.

The at least one physical parameter value in the methods, computer product programs and device as described herein may be selected from one of a group including but not limited to: surface/interface tension; surface/interface viscosity; surface/interface elasticity; final break-up time; relaxation time; shear viscosity and extensional viscosity. The inventors hypothesise that there is a correlation between tear viscoelasticity measures (including surface/interface tension, surface/interface viscosity, surface/interface elasticity, final break-up time, relaxation time, shear viscosity and extensional viscosity) and clinical diagnosis of DED. In some embodiments, the at least one physical parameter value manifests as an apparent viscosity or extensional viscosity based on the extensional measurement obtained using the ADMiER instrument. The possible correlation between apparent viscosity measures and clinical diagnosis of DED is discussed below in Examples 1 and 2. The inventors hypothesise that similar correlations apply to other tear viscoelasticity measures as described herein.

The inventive methods, computer product programs and device provide novel diagnostic modalities for relatively reliably and relatively accurately evaluating DED in a human or animal subject. The novel diagnostic methods performed are relatively simple, relatively rapid and objective, and enable measurement of a single physical parameter to capture the subject's tear film status and evaluate DED. Further physical parameters may be used to provide additional information about the DED diagnosis. Advantageously, the inventive methods, computer product programs and device involve the use of an ADMiER instrument to quantify the viscoelastic properties of a human or animal tear sample. In contrast to certain of the prior art, the ADMiER instrument is able to consistently form capillary bridges for low viscosity fluids from microlitre tear samples in order to provide objective and robust measurement of tear film capillary thinning. Furthermore, no or minimal consumables are required which greatly reduce the testing cost in contrast to certain prior art diagnostic modalities.

It is to be understood that various modifications, additions and/or alternatives may be made to the parts previously described without departing from the ambit of the present disclosure as defined in the claims appended hereto.

Where any or all of the terms "comprise", "comprises", "comprised" or "comprising" are used in this specification (including the claims) they are to be interpreted as specifying the presence of the stated features, integers, steps or components, but not precluding the presence of one or more other features, integers, steps or components.

Examples illustrating applications of embodiments of the disclosure will now be described. The examples are supplied to provide context and explain features and advantages of the disclosure and are not limiting on the scope of the disclosure as defined in the claims.

Example 1

In a study involving 11 adults (22 eyes), tear film status was graded on the basis of tear osmolarity findings into one of three categories: 'healthy' (<308 mOsmol/L), 'borderline' (308-315 mOsmol/L) or 'dry' (≥316 mOsmol/L). Basal tear samples (~2 µl per eye) were non-invasively collected using a glass microcapillary tube and immediately analysed using the ADMiER instrument, to derive tear viscoelasticity measures. To characterise the clinical expression of DED, a series of standard dry eye diagnostic tests were performed as follows:

TABLE 1

Diagnostic test accuracy study assessments

| Test parameter | Description |
| --- | --- |
| Dry eye Symptoms (/100) | Dry eye symptoms quantified using the Ocular Surface Disease Index (OSDI, Allergan Inc.), being a validated, standardised dry eye questionnaire. |
| Tear osmolarity (mOsmol/L) | Reference test: Tear osmolarity assayed using the TearLab ™ system, which collects and analyses a 50 nL tear sample from the infero-lateral canthus. To ensure measurement accuracy, room temperature was strictly maintained at $20 \pm 4^1$ C., with daily calibration. |
| Tear stability: (seconds) | Non-invasive tear break-up-time (NITBUT) measured 3 times per eye using the Placido-disc based Tear Film Surface Quality (TFSQ) index with the Medmont E300 corneal topographer. |
| Tear viscoelasticity (Pa · s) | Index test: A 2 µl basal tear sample non-invasively collected from the lateral canthus using a glass microcapillary tube and immediately analysed using the ADMiER platform to derive tear apparent viscosity measures. Tear flow rate monitored to exclude potential tear dilution effects caused by reflex tearing. Samples with a flow rate of 1-5 µl/min were considered consistent with basal tears. |
| Slit lamp Examination | A slit lamp examination, using 10x and 16x magnification, undertaken to assess corneal integrity (in particular to examine for the presence of active inflammation or structural abnormalities). The iris and anterior chamber examined using the SUN criteria for inflammation. The extent of any anterior blepharitis graded using the Efron scale. |
| Tear stability: invasive (seconds) | TBUT: 1-2 µL sodium fluorescein (NaFl) instilled into each eye using Dry Eye Test strips. TBUT manually measured using a stopwatch, for 3 consecutive repeated measures per eye, at the slit lamp biomicroscope with a Wratten 12 barrier filter. |
| Total ocular surface staining (/15.0) | Ocular surface staining quantified as the sum of the corneal NaFl staining score/5.0 (graded under 16x magnification with Cobalt blue illumination and a yellow barrier filter, one minute after NaFl instillation) and the nasal + temporal conjunctival lissamine green (LG) staining score/10.0 |

TABLE 1-continued

Diagnostic test accuracy study assessments

| Test parameter | Description |
| --- | --- |
| | (graded under 16x magnification with diffuse white illumination, 3 mins after LG instillation). Each ocular surface region graded in 0.1 increments using the Oxford scale. |
| Meibomian gland evaluation | Meibomian gland integrity, to assess for evaporative dry eye, evaluated by grading the quality of meibum, level of gland expressibility and volume of gland secretion, using the Bron/Foulks scoring system. |
| Tear production | The Schirmer test used to assess aqueous-deficient dry eye using a standard clinical protocol. The extent of strip wetting (in mm) is measured after 5 mins, following topical anaesthesia. |

Figures 16A, 16B:
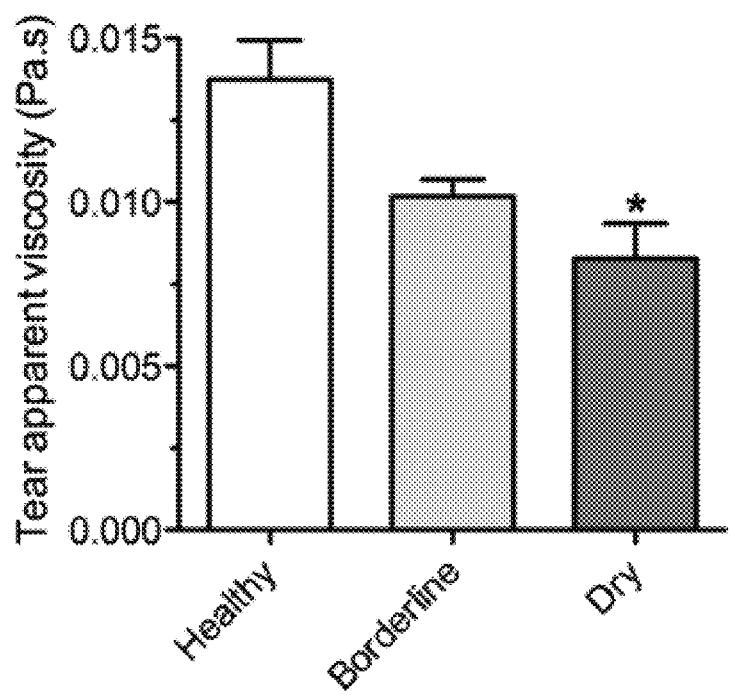
FIG. 16A shows results from a series of standard diagnostic tests for DED pertaining to Example 1.
FIG. 16B is a chart showing results of tear apparent viscosity measurements for clinical diagnosis of tear film status pertaining to Example 1.

FIG. 16A shows the results from the series of standard dry eye diagnostic tests performed according to the protocols outlined in Table 1. The factor 'n' refers to the number of eyes included in the analyses and the data is shown as mean±SEM with * symbol representing $p<0.05$. As expected, significant differences between clinical parameters were evident between 'healthy' and 'dry' eyes (see FIG. 16A), the latter showing relatively higher tear osmolarity, reduced tear stability (NITBUT and NaFl TBUT), higher levels of ocular surface staining and reduced tear production ($p<0.05$ for all comparisons).

Analysis of group tear viscoelasticity data showed significantly lower apparent viscosity in dry eyes compared with healthy eyes as shown in the chart of FIG. 16B. The data is shown as mean±SEM with * symbol representing $p<0.05$. The representative ranges of tear apparent viscosity for the categories of tear film status were as follows: 'healthy' tears 0.011506 Pa·s to 0.02266 Pa·s; 'borderline' tears 0.007857 Pa·s to 0.011506 Pa·s; and 'dry' tears 0.005973 Pa·s to 0.007857 Pa·s. The inventors found that using an apparent viscosity cut-off criterion of 0.00873 Pa·s yields 83% potential sensitivity and 94% specificity for diagnosing the presence of DED.

Accordingly, the study provides representative ranges and threshold values of apparent tear viscosity that may be used for diagnosing the presence and assessing the severity of DED. In particular, the range of reference values indicative of the presence of DED may include the range of 0.0059 Pa·s to 0.0115 Pa·s. The range of reference values indicative of definitive DED ('dry' tears) may include the range of 0.0059 Pa·s to 0.0079 Pa·s. Further, the range of reference values indicative of borderline DED may include the range of 0.0079 Pa·s to 0.0115 Pa·s. DED may also be diagnosed when the measured tear apparent viscosity is less than threshold values of 0.0115 Pa·s and more preferably, 0.00873 Pa·s. Furthermore, definitive DED ('dry' tears) may be assessed when the measured tear apparent viscosity is less than the threshold value of 0.0079 Pa·s, otherwise the severity of DED is assessed as borderline DED.

The finding that tear viscoelasticity is compromised in DED is consistent with the rationale for the most common DED treatment modality, involving the instillation of relatively viscous, synthetic tear supplements to increase tear retention. The inventors conducted assays of several artificial tear products with the ADMiER instrument confirming that their viscoelasticities exceed that of healthy tears (data not shown). The data supports the hypothesis that there is a possible correlation between the apparent viscosity value of tear samples and clinical diagnosis of DED.

Figure 17:
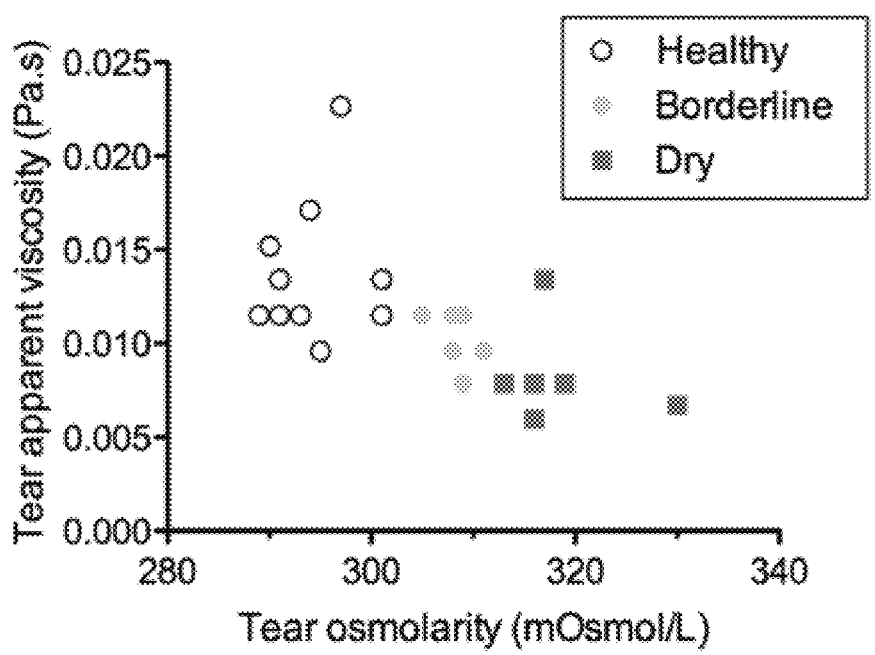
FIG. 17 is a chart showing results of a relationship between tear apparent viscosity and osmolarity pertaining to Example 1.

Tear hyperosmolarity is considered to be the preferred indicator of DED severity although it cannot differentiate between different DED sub-types. The inventors hypothesise that more severe clinical expressions of DED are associated with greater reductions in tear apparent viscosity (i.e., poorer overall tear film viscoelasticity). Supporting this hypothesis is data from the study of 22 eyes which is presented in the chart of FIG. 17 plotting tear apparent viscosity against tear osmolarity. The inventors found a moderately strong negative correlation (Spearman's correlation co-efficient: $r=-0.65$, $p=0.0008$) between tear apparent viscosity and tear osmolarity. Accordingly, the inventors hypothesise that differences will exist in tear apparent viscosity between samples from predominately evaporative versus aqueous-deficient dry eyes as a consequence of divergent changes to tear film integrity that occur in each disease sub-type (i.e., reduced aqueous versus altered lipids).

Figure 18:
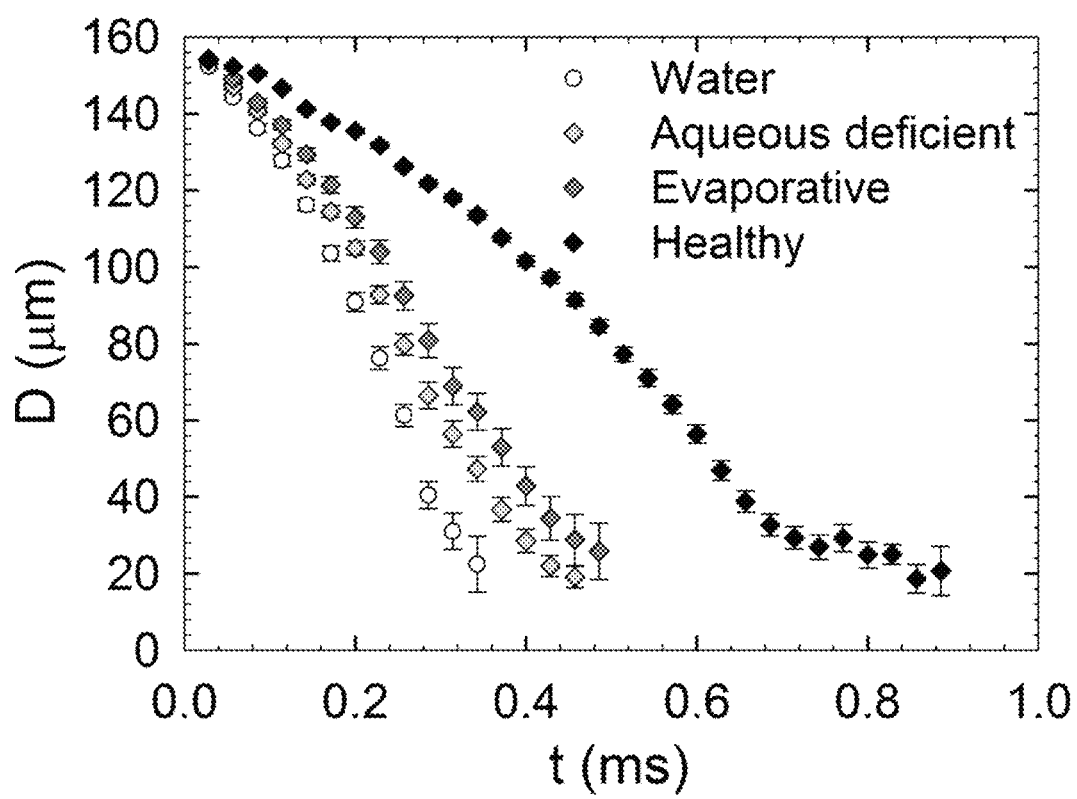
FIG. 18 is a chart showing results of filament thinning for aqueous deficient DED, evaporative DED and healthy tear films pertaining to Example 1.

FIG. 18 is a chart providing filament break-up data from the study of 22 eyes that suggests potential differences in decay of filament thinning between clinically-defined aqueous-deficient and evaporative DED. Definite aqueous-deficient DED was defined by the presence of significant tear hyperosmolarity ($\geq 316$ mOsmol/L), in association with a Schirmer strip test measurement of 5 mm or less in 5 mins. Definite evaporative DED was defined by the presence of significant tear hyperosmolarity ($\geq 316$ mOsmol/L), in association with a Schirmer strip test measurement of at least 10 mm in 5 mins and evidence of meibomian gland dysfunction (considered as at least Grade 2 findings in one or more of: quality of meibum, level of gland expressibility and volume of gland secretion using the Bron/Foulks scoring system).

FIG. 18 indicates that shorter decays occur in less viscous unhealthy tears, suggesting the absence of constituents otherwise seen in healthy samples. The inventors have also quantified significant differences in the viscoelastic properties of tear supplemental products marketed specifically for these sub-types (data not shown). Together, the data supports the hypothesis that tear viscoelasticity assays may be useful in assessing the severity of DED and/or for differentiating between its clinical sub-types.

Example 2

A cross-sectional study was performed to assess diagnostic test accuracy in using tear extensional viscosity measurements obtained using ADMiER to diagnose DED (presence of DED or no presence of DED), assess the severity of DED (definitive or borderline DED) and classify DED into its predominant clinical sub-types (aqueous deficient or evaporative DED). The study involved a primary eye care population of 78 adults (156 eyes) with a mean±standard deviation (SD) age of 32±12 years (range of 18-77 years) and gender of 69% female.

Figures 19A, 19B:
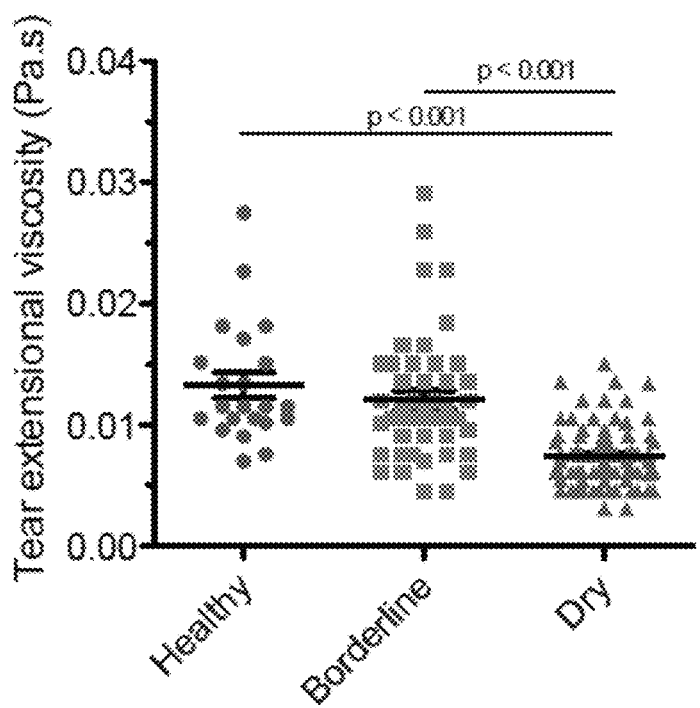
FIG. 19A shows results from a series of standard diagnostic tests for DED and tear extensional viscosity measurements pertaining to Example 2.
FIG. 19B is a chart showing results of tear extensional viscosity measurements for clinical diagnosis of tear film status pertaining to Example 2.

FIG. 19A shows summary results from a series of standard dry eye diagnostic tests for DED performed based on the protocols outlined in Table 1 and tear extensional viscosity measurements made using ADMiER. A clinical dry eye severity score (0.0 to 4.0) was objectively derived using standardised dry eye questionnaires (Ocular Surface Disease Index ("OSDI") and Standardized Patient Evaluation of Eye Dryness ("SPEED")) and clinical signs of DED (as determined by a compound score relating to the combination of findings from a comprehensive slit lamp examination, assessment of ocular redness, sodium fluorescein tear break-up time, corneal sodium fluorescein staining, conjunctival lissamine green staining, meibomian gland evaluation and Schirmer test score). The score (from 0.0 to 4.0) was based upon the DEWS (2007) Diagnostic Methodology sub-committee classification. Clinically significant DED was referenced by a clinical dry eye score of 1.0 or greater. The factor 'n' refers to the number of eyes in the analyses and the data is shown as mean±SD. Similar to Example 1, statistically significant differences between clinical parameters were evident between 'healthy' and 'dry' eyes, the latter showing higher clinical dry eye severity score, reduced tear stability ("TBUT") and reduced tear production (Schirmer test).

Analysis of group tear extensional viscosity data showed statistically significant lower extensional viscosity values in definitive 'dry' eyes compared to 'healthy' and 'borderline' eyes as shown in the chart of FIG. 19B (p<0.0001). The mean±SD tear extensional viscosity values for the categories of tear film status were as follows: 'healthy' tears 0.0133±0.005 Pa·s; 'borderline' tears 0.012±0.005 Pa·s; and 'dry' tears 0.007±0.003 Pa·s as shown in FIG. 19A. The representative ranges of tear extensional viscosity values for the categories of tear film status were as follows: 'healthy' tears 0.00699 Pa·s to 0.0275 Pa·s; 'borderline' tears 0.00455 Pa·s to 0.029 Pa·s; and 'dry' tears 0.00307 Pa·s to 0.0151 Pa·s.

Figure 20:
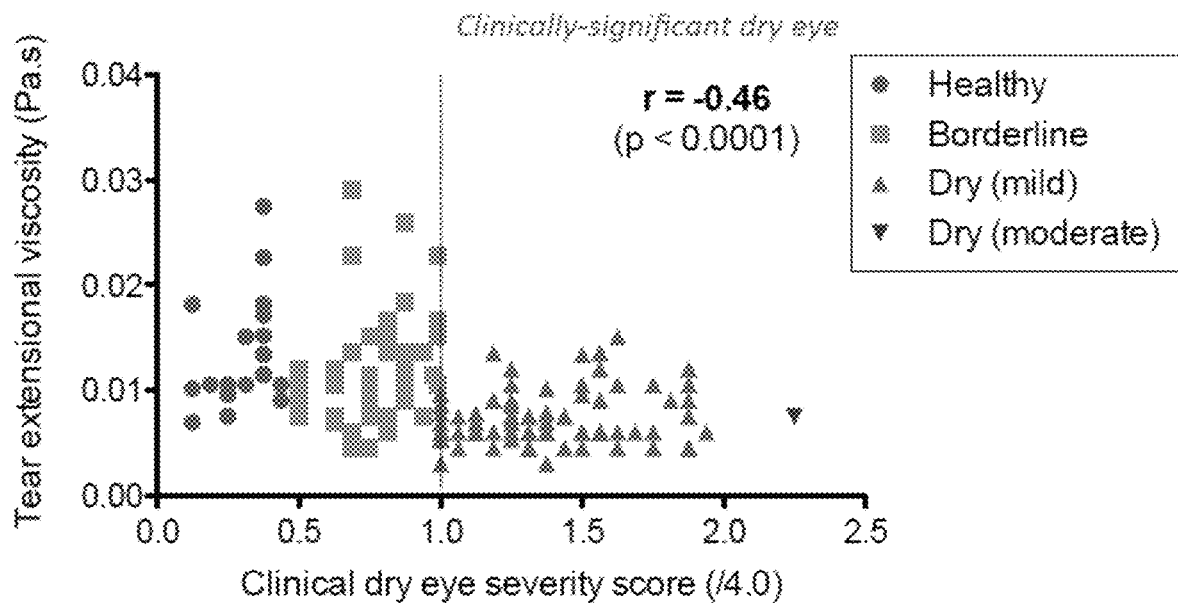
FIG. 20 is a chart showing results of a relationship between tear extensional viscosity and clinical dry eye severity score pertaining to Example 2.

FIG. 20 is a chart showing results of a relationship between tear extensional viscosity and clinical dry eye severity score for this study. The inventors found a moderately negative correlation (Spearman's correlation co-efficient: r=−0.46, p<0.0001) between tear extensional viscosity and clinical dry eye severity score. There was a statistically significant correlation between low tear extensional viscosities and mild or moderate severity of DED for clinical dry eye severity scores of greater than 1.0. Accordingly, lower tear extensional viscosities are indicative of more severe DED.

Figure 21:
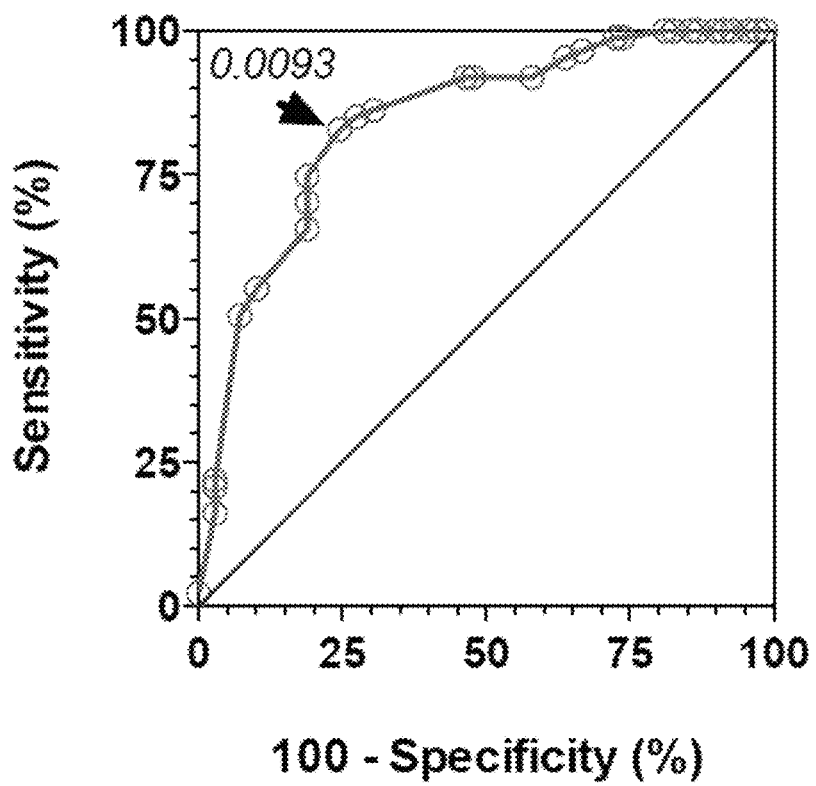
FIG. 21 is a chart showing Receiver Operator Characteristic ("ROC") curve analysis of the data pertaining to Example 2.
Figure 22:
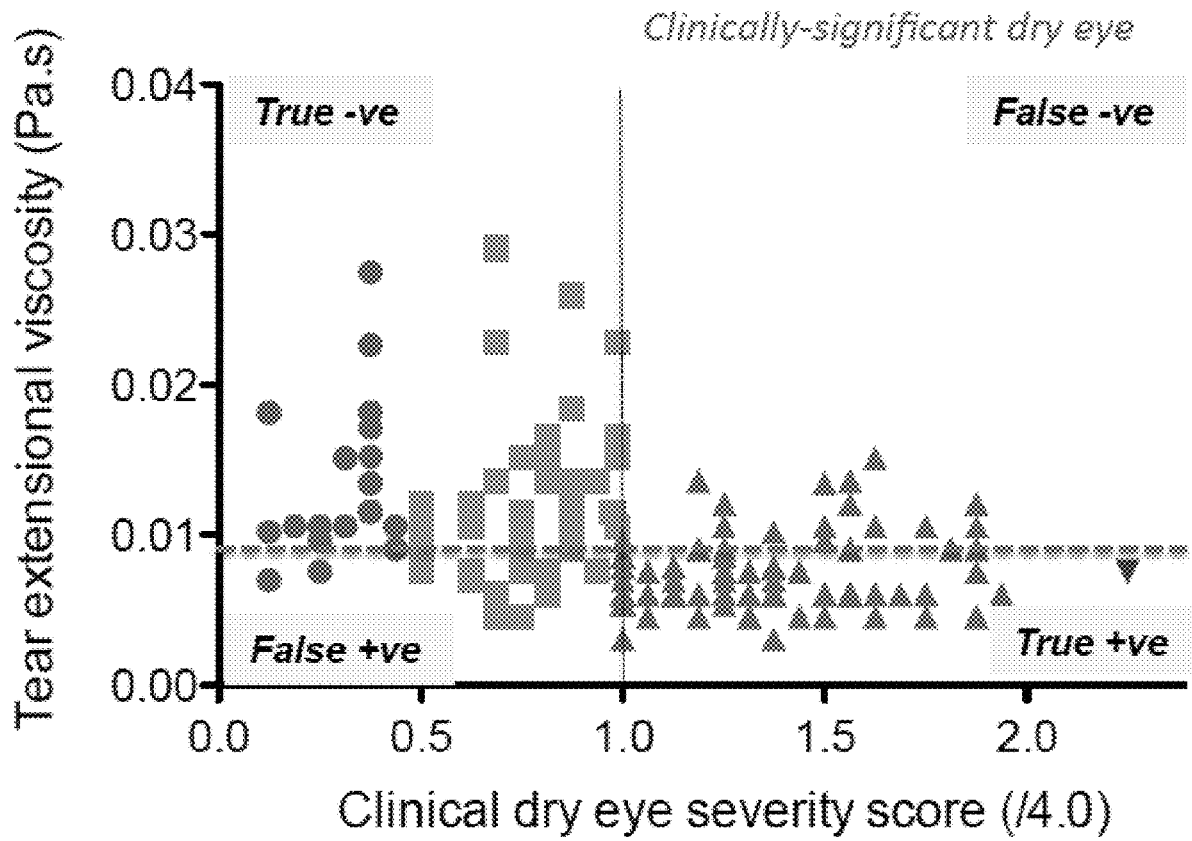
FIG. 22 shows the chart of FIG. 20 indicating an exemplary tear extensional viscosity threshold value for diagnosing the presence of DED.

FIG. 21 is a chart showing Receiver Operator Characteristic ("ROC") curve analysis for this study. The analysis revealed that a cut-off criterion of 0.0093 Pa·s yields 83% sensitivity and 75% specificity for diagnosing the presence of DED (dry' tears versus 'healthy' and 'borderline' tears combined). The Area Under Curve ("AUC") was 0.84, 95% Confidence Limit ("CI") of 0.78 to 0.91 (p<0.0001). FIG. 22 shows the chart of FIG. 20 indicating the exemplary tear extensional viscosity value for diagnosing DED. The positive predictive value for DED was 81% and the negative predictive value for DED was 78%.

Accordingly, the study provides representative ranges and threshold values of extensional viscosity that may be used for diagnosing the presence and assessing the severity of DED. The range of reference values indicative of the presence of DED may include the range of about 0.0031 Pa·s to about 0.0151 Pa·s, and more specifically in the range of about 0.0059 Pa·s to about 0.0115 Pa·s. The range of reference values indicative of definitive DED ('dry' tears) may include the range of about 0.0031 Pa·s to about 0.0151 Pa·s, and more specifically in the range of about 0.0059 Pa·s to about 0.0079 Pa·s. Further, the range of reference values indicative of borderline DED may include the range of about 0.00455 Pa·s to 0.0259 Pa·s and more specifically in the range of about 0.0079 Pa·s to about 0.0115 Pa·s. DED may also be diagnosed when the measured tear extensional viscosity is less than threshold value of about 0.0093 Pa·s. Furthermore, definitive DED ('dry' tears) may be assessed when the measured tear extensional viscosity is less than the threshold value of about 0.0093 Pa·s, otherwise the tears are assessed as healthy or borderline.

Figure 23:
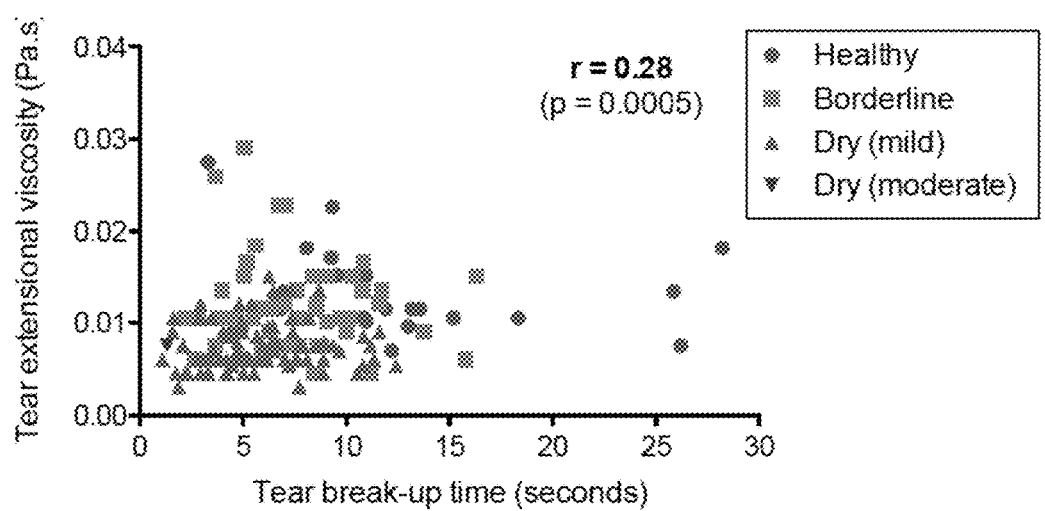
FIG. 23 is a chart showing results of a relationship between tear extensional viscosity and tear break-up time pertaining to Example 2.

FIG. 23 is a chart showing results of a relationship between tear extensional viscosity and sodium fluorescein tear break-up time ("TBUT") for this study. The inventors found a modest positive correlation (Spearman's correlation co-efficient: r=0.28, p=0.0005) between tear extensional viscosity and TBUT. Accordingly, tear extensional viscosity shows a statistically significant correlation with clinically-defined tear stability ("TBUT").

Figure 24:
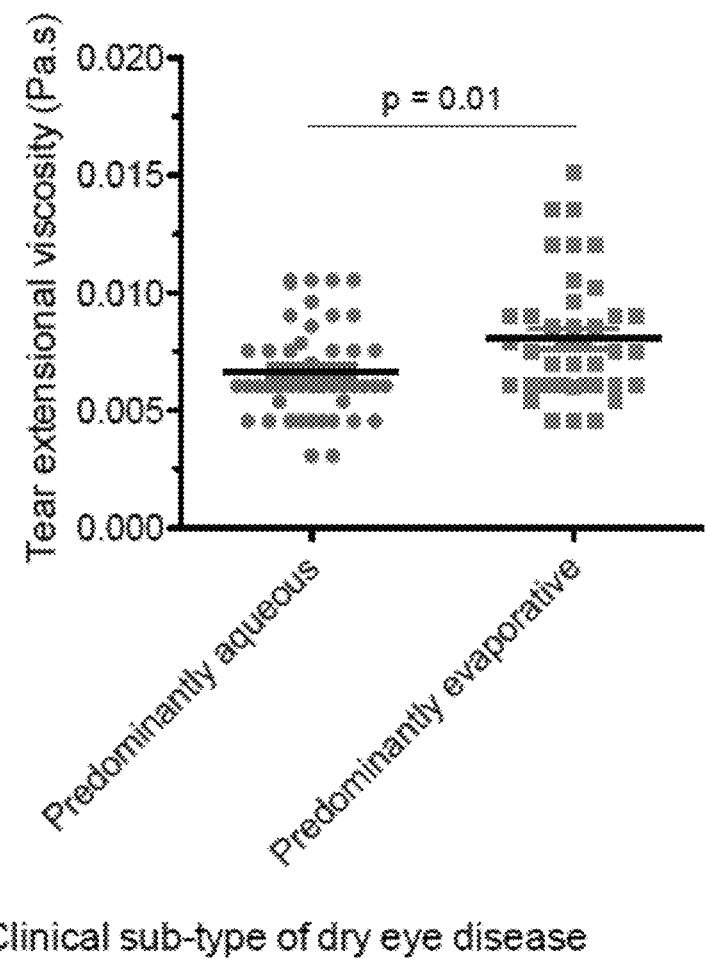
FIG. 24 is a chart showing results of tear extensional viscosity measurements for classifying a predominant clinical sub-type of DED pertaining to Example 2.

FIG. 24 is a chart showing results of tear extensional viscosity measurements from this study for classifying the predominant clinical sub-type of DED as aqueous deficient DED or evaporative DED. The inventors found a statistically significant difference in the mean tear extensional viscosity values between predominately aqueous deficient and evaporative eyes, the latter showing higher average tear extensional viscosity values (p=0.01). Accordingly, tear extensional viscosity is lower in predominantly aqueous deficient eyes compared with predominantly evaporative dry eyes.

Figure 25:
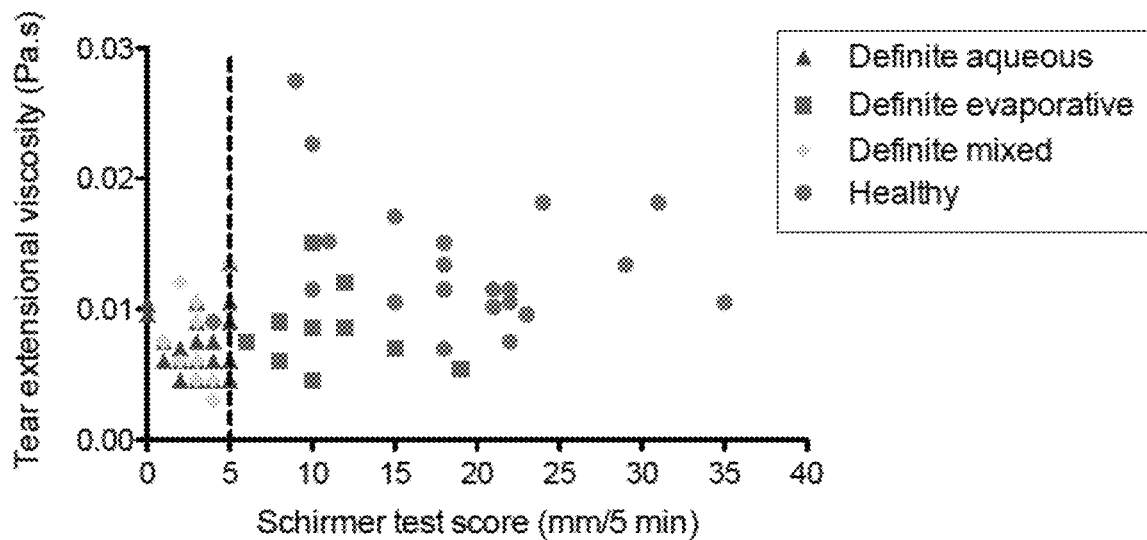
FIG. 25 is a chart showing results of a relationship between tear extensional viscosity and Schirmer test score pertaining to Example 2.

FIG. 25 is a chart showing results of a relationship between tear extensional viscosity and the Schirmer test score to differentiate between clinical sub-types of DED. The inventors found a modest positive correlation (Spearman's correlation co-efficient: r=0.22, p=0.006) between tear extensional viscosity and Schirmer test score. Schirmer test score values of 5 mm/5 min or less show a statistically significant difference in extensional viscosity for definite aqueous deficient DED and evaporative DED. In particular, definitive evaporative DED is associated with higher tear extensional viscosity values than definite aqueous deficient DED and Schirmer test scores of more than 5 mm/5 min.

Analysis of group extensional viscosity data shows that the mean±SD tear extensional viscosity for the categories of tear film status were as follows: 'predominantly aqueous' (n=47) tears 0.00665±0.002 Pa·s; and 'predominantly evaporative' (n=40) tears 0.00807±0.003 Pa·s. The representative ranges of tear extensional viscosity for the clinical sub-type of DED were as follows: 'predominantly aqueous' tears 0.00307 Pa·s to 0.0105 Pa·s; and 'predominantly evaporative' tears 0.00455 Pa·s to 0.0151 Pa·s.

Accordingly, the study provides representative ranges and threshold values of extensional viscosity that may be used for classifying sub-types of DED. The range of reference values indicative of predominantly aqueous deficient DED may include the range of 0.00307 Pa·s to 0.0105 Pa·s. The range of reference values indicative of predominantly evaporative DED may include the range of 0.00455 Pa·s to 0.0151 Pa·s. Further, aqueous deficient DED may be classified when the measured tear extensional viscosity is less than the threshold value of about 0.00651 Pa·s, otherwise the clinical sub-type is classified as evaporative DED.

It is to be understood that the following claims are provided by way of example only, and are not intended to limit the scope of what may be claimed in any future application. Features may be added to or omitted from the claims at a later date so as to further define or re-define the disclosure or disclosures.

The invention claimed is:

1. A method for evaluating Dry Eye Disease in a human or animal subject, the method comprising:
   determining thread thinning dynamics of a tear sample of the subject using an acoustically-driven microfluidic extensional rheometry instrument, wherein the determined thread thinning dynamics comprise at least one extensional viscosity measurement of the tear sample;
   calculating at least one physical parameter value of the tear sample based at least in part on the at least one extensional viscosity measurement of the determined thread thinning dynamics of the tear sample, wherein the calculated at least one physical parameter value is selected from the group consisting of: a surface/interface tension; a surface/interface viscosity; a surface/interface elasticity; a final break-up time; a relaxation time; and an extensional viscosity;
   evaluating Dry Eye Disease based at least in part on the calculated at least one physical parameter value of the tear sample, wherein evaluating Dry Eye Disease comprises:
      comparing the at least one physical parameter value with one or more reference values for evaluating Dry Eye Disease; and
      evaluating Dry Eye Disease based on the comparison of the at least one physical parameter value with the one or more reference values for evaluating Dry Eye Disease; and
   based on the comparison of the at least one physical parameter value with the one or more reference values for evaluating Dry Eye Disease, one or more of:
      diagnosing a presence of Dry Eye Disease, wherein the presence of Dry Eye Disease is diagnosed when an extensional viscosity value of the tear sample is within the range of 0.0001 Pa·s to 0.025 Pa·s;
      assessing a severity of Dry Eye Disease; and
      identifying a clinical sub-type of Dry Eye Disease.

2. The method of claim 1, wherein determining thread thinning dynamics comprises:
   obtaining thread thinning data of the tear sample using the acoustically-driven microfluidic extensional rheometry instrument by:
      forming a fluid capillary bridge of the tear sample using the acoustically-driven microfluidic extensional rheometry instrument; and
      measuring changes in radius along the fluid capillary bridge during thread thinning; and
   analysing the thread thinning data to determine the thread thinning dynamics.

3. The method of claim 2, wherein forming a fluid capillary bridge comprises:
   providing the acoustically-driven microfluidic extensional rheometry instrument with:
      opposing plates between which a fluid capillary bridge can be formed, and
      an acoustic wave actuator having a working surface located on one of the plates, wherein the acoustic wave actuator is configured to use at least one of: surface acoustic waves, bulk waves, and surface reflected bulk waves;
   applying the tear sample to the working surface of the acoustic wave actuator; and
   energising the acoustic wave actuator to produce the fluid capillary bridge of the tear sample between the plates.

4. The method of claim 1, further comprising providing one or more outcomes of the evaluation of Dry Eye Disease, wherein the one or more outcomes include:
   a presence of Dry Eye Disease;
   a borderline Dry Eye Disease or a definitive Dry Eye Disease;
   a mild, a moderate or a severe definitive Dry Eye Disease;
   an aqueous deficient Dry Eye Disease and/or an evaporative Dry Eye Disease; and
   a predominant aqueous deficient Dry Eye Disease or a predominant evaporative Dry Eye Disease.

5. A device configured to evaluate Dry Eye Disease in a human or animal subject, the device comprising:
   an acoustically-driven microfluidic extensional rheometry instrument; and
   a processing device configured to:
      determine thread thinning dynamics of a tear sample of the subject using the acoustically-driven microfluidic extensional rheometry instrument, wherein the determination includes receiving thread thinning data of the tear sample obtained using the acoustically-driven microfluidic extensional rheometry instrument, and analysing the thread thinning data to determine the thread thinning dynamics, wherein the determined thread thinning dynamics comprise at least one extensional viscosity measurement of the tear sample;
      calculate at least one physical parameter value of the tear sample based at least in part on the at least one extensional viscosity measurement of the determined thread thinning dynamics of the tear sample;
      evaluate Dry Eye Disease based at least in part on the calculated at least one physical parameter value of the tear sample and by:
         comparing the at least one physical parameter value with one or more reference values for evaluating Dry Eye Disease, wherein the at least one physical parameter value is selected from the group consisting of: a surface/interface tension; a surface/interface viscosity; a surface/interface elasticity; a final break-up time; a relaxation time; and an extensional viscosity; and
         evaluating Dry Eye Disease based on the comparison of the at least one physical parameter value with the one or more reference values for evaluating Dry Eye Disease; and
      based on the comparison of the at least one physical parameter value with the one or more reference values for evaluating Dry Eye Disease, one or more of:
         diagnose a presence of Dry Eye Disease, wherein the presence of Dry Eye Disease is diagnosed when an extensional viscosity value of the tear sample is within the range of 0.0001 Pa·s to 0.025 Pa·s;
         assess a severity of Dry Eye Disease; and
         identify a clinical sub-type of Dry Eye Disease.

6. The device of claim 5, wherein the thread thinning data includes changes in radius along a fluid capillary bridge of the tear sample during thread thinning, wherein the fluid capillary bridge is formed using the acoustically-driven microfluidic extensional rheometry instrument.

7. The device of claim 6, wherein the acoustically-driven microfluidic extensional rheometry instrument includes:
   opposing plates between which the fluid capillary bridge is formable; and
   an acoustic wave actuator having a working surface located on one of the plates, wherein the acoustic wave actuator is configured to use at least one of: surface acoustic waves, bulk waves, and surface reflected bulk waves, and wherein when the tear sample is applied to the working surface of the acoustic wave actuator, and the acoustic wave actuator is energized, the fluid capillary bridge of the tear sample is produced between the plates.

8. A method for evaluating Dry Eye Disease in a human or animal subject, the method comprising:

determining thread thinning dynamics of a tear sample of the subject using an acoustically-driven microfluidic extensional rheometry instrument, wherein the determined thread thinning dynamics comprise at least one extensional viscosity measurement of the tear sample;

calculating at least one physical parameter value of the tear sample based at least in part on the at least one extensional viscosity measurement of the determined thread thinning dynamics of the tear sample, wherein the calculated at least one physical parameter value is selected from the group consisting of: a surface/interface tension; a surface/interface viscosity; a surface/interface elasticity; a final break-up time; a relaxation time; and an extensional viscosity;

evaluating Dry Eye Disease based at least in part on the calculated at least one physical parameter value of the tear sample, wherein evaluating Dry Eye Disease comprises:

comparing the at least one physical parameter value with one or more reference values for evaluating Dry Eye Disease; and evaluating Dry Eye Disease based on the comparison of the at least one physical parameter value with the one or more reference values for evaluating Dry Eye Disease; and based on the comparison of the at least one physical parameter value with the one or more reference values for evaluating Dry Eye Disease, one or more of:

diagnosing a presence of Dry Eye Disease;

assessing a severity of Dry Eye Disease, wherein assessing the severity of Dry Eye Disease includes classifying the severity as borderline Dry Eye Disease or definitive Dry Eye Disease, the severity is classified as definitive Dry Eye Disease when an extensional viscosity value of the tear sample is within the range of 0.0031 Pa·s to 0.0151 Pa·s, otherwise the severity is classified as borderline Dry Eye Disease; and identifying a clinical sub-type of Dry Eye Disease.

9. The method of claim 8, wherein determining thread thinning dynamics comprises:

obtaining thread thinning data of the tear sample using the acoustically-driven microfluidic extensional rheometry instrument by:

forming a fluid capillary bridge of the tear sample using the acoustically-driven microfluidic extensional rheometry instrument; and measuring changes in radius along the fluid capillary bridge during thread thinning; and analysing the thread thinning data to determine the thread thinning dynamics.

10. The method of claim 9, wherein forming a fluid capillary bridge comprises:

providing the acoustically-driven microfluidic extensional rheometry instrument with:

opposing plates between which a fluid capillary bridge can be formed, and an acoustic wave actuator having a working surface located on one of the plates, wherein the acoustic wave actuator is configured to use at least one of: surface acoustic waves, bulk waves, and surface reflected bulk waves;

applying the tear sample to the working surface of the acoustic wave actuator; and energising the acoustic wave actuator to produce the fluid capillary bridge of the tear sample between the plates.

11. The method of claim 8, further comprising providing one or more outcomes of the evaluation of Dry Eye Disease, wherein the one or more outcomes include:

a presence of Dry Eye Disease;

a borderline Dry Eye Disease or a definitive Dry Eye Disease;

a mild, a moderate or a severe definitive Dry Eye Disease;

an aqueous deficient Dry Eye Disease and/or an evaporative Dry Eye Disease; and a predominant aqueous deficient Dry Eye Disease or a predominant evaporative Dry Eye Disease.

12. A method for evaluating Dry Eye Disease in a human or animal subject, the method comprising:

determining thread thinning dynamics of a tear sample of the subject using an acoustically-driven microfluidic extensional rheometry instrument, wherein the determined thread thinning dynamics comprise at least one extensional viscosity measurement of the tear sample;

calculating at least one physical parameter value of the tear sample based at least in part on the at least one extensional viscosity measurement of the determined thread thinning dynamics of the tear sample, wherein the calculated at least one physical parameter value is selected from the group consisting of: a surface/interface tension; a surface/interface viscosity; a surface/interface elasticity; a final break-up time; a relaxation time; and an extensional viscosity;

evaluating Dry Eye Disease based at least in part on the calculated at least one physical parameter value of the tear sample, wherein evaluating Dry Eye Disease comprises:

comparing the at least one physical parameter value with one or more reference values for evaluating Dry Eye Disease; and evaluating Dry Eye Disease based on the comparison of the at least one physical parameter value with the one or more reference values for evaluating Dry Eye Disease; and based on the comparison of the at least one physical parameter value with the one or more reference values for evaluating Dry Eye Disease, one or more of:

diagnosing a presence of Dry Eye Disease;

assessing a severity of Dry Eye Disease; and identifying a clinical sub-type of Dry Eye Disease, wherein identifying a clinical sub-type of Dry Eye Disease includes classifying the clinical sub-type of Dry Eye Disease as one or both of aqueous deficient Dry Eye Disease and evaporative Dry Eye Disease, wherein one of:

the clinical sub-type is classified as aqueous deficient Dry Eye Disease when an extensional viscosity value of the tear sample is less than 0.00651 Pa·s, otherwise the clinical sub-type is classified as evaporative Dry Eye Disease, or the clinical sub-type is classified as aqueous deficient Dry Eye Disease when an extensional viscosity value of the tear sample is in the range of 0.00307 Pa·s to 0.0105 Pa·s and the clinical sub-type is classified as evaporative Dry Eye Disease when an extensional viscosity value of the tear sample is in the range of 0.00455 Pa·s to 0.0151 Pa·s.

13. The method of claim 12, wherein determining thread thinning dynamics comprises:
   obtaining thread thinning data of the tear sample using the acoustically-driven microfluidic extensional rheometry instrument by:
      forming a fluid capillary bridge of the tear sample using the acoustically-driven microfluidic extensional rheometry instrument; and
      measuring changes in radius along the fluid capillary bridge during thread thinning; and
   analysing the thread thinning data to determine the thread thinning dynamics.

14. The method of claim 13, wherein forming a fluid capillary bridge comprises:
   providing the acoustically-driven microfluidic extensional rheometry instrument with:
      opposing plates between which a fluid capillary bridge can be formed, and
      an acoustic wave actuator having a working surface located on one of the plates, wherein the acoustic wave actuator is configured to use at least one of: surface acoustic waves, bulk waves, and surface reflected bulk waves;
   applying the tear sample to the working surface of the acoustic wave actuator; and
   energising the acoustic wave actuator to produce the fluid capillary bridge of the tear sample between the plates.

15. The method of claim 12, further comprising providing one or more outcomes of the evaluation of Dry Eye Disease, wherein the one or more outcomes include:
   a presence of Dry Eye Disease;
   a borderline Dry Eye Disease or a definitive Dry Eye Disease;
   a mild, a moderate or a severe definitive Dry Eye Disease;
   an aqueous deficient Dry Eye Disease and/or an evaporative Dry Eye Disease; and
   a predominant aqueous deficient Dry Eye Disease or a predominant evaporative Dry Eye Disease.

16. A device configured to evaluate Dry Eye Disease in a human or animal subject, the device comprising:
   an acoustically-driven microfluidic extensional rheometry instrument; and
   a processing device configured to:
      determine thread thinning dynamics of a tear sample of the subject using the acoustically-driven microfluidic extensional rheometry instrument, wherein the determination includes receiving thread thinning data of the tear sample obtained using the acoustically-driven microfluidic extensional rheometry instrument, and analysing the thread thinning data to determine the thread thinning dynamics, wherein the determined thread thinning dynamics comprise at least one extensional viscosity measurement of the tear sample;
      calculate at least one physical parameter value of the tear sample based at least in part on the at least one extensional viscosity measurement of the determined thread thinning dynamics of the tear sample;
      evaluate Dry Eye Disease based at least in part on the calculated at least one physical parameter value of the tear sample and by:
         comparing the at least one physical parameter value with one or more reference values for evaluating Dry Eye Disease, wherein the at least one physical parameter value is selected from the group consisting of: a surface/interface tension; a surface/interface viscosity; a surface/interface elasticity; a final break-up time; a relaxation time; and an extensional viscosity; and
         evaluating Dry Eye Disease based on the comparison of the at least one physical parameter value with the one or more reference values for evaluating Dry Eye Disease; and
      based on the comparison of the at least one physical parameter value with the one or more reference values for evaluating Dry Eye Disease, one or more of:
         diagnose a presence of Dry Eye Disease;
         assess a severity of Dry Eye Disease by classifying the severity as borderline Dry Eye Disease or definitive Dry Eye Disease, wherein the severity is classified as definitive Dry Eye Disease when an extensional viscosity value of the tear sample is within the range of 0.0031 Pa·s to 0.0151 Pa·s, otherwise the severity is classified as borderline Dry Eye Disease; and
         identify a clinical sub-type of Dry Eye Disease.

17. The device of claim 16, wherein the thread thinning data includes changes in radius along a fluid capillary bridge of the tear sample during thread thinning, wherein the fluid capillary bridge is formed using the acoustically-driven microfluidic extensional rheometry instrument.

18. The device of claim 17, wherein the acoustically-driven microfluidic extensional rheometry instrument includes:
   opposing plates between which the fluid capillary bridge is formable; and
   an acoustic wave actuator having a working surface located on one of the plates, wherein the acoustic wave actuator is configured to use at least one of: surface acoustic waves, bulk waves, and surface reflected bulk waves, and
   wherein when the tear sample is applied to the working surface of the acoustic wave actuator, and the acoustic wave actuator is energized, the fluid capillary bridge of the tear sample is produced between the plates.

19. A device configured to evaluate Dry Eye Disease in a human or animal subject, the device comprising:
   an acoustically-driven microfluidic extensional rheometry instrument; and
   a processing device configured to:
      determine thread thinning dynamics of a tear sample of the subject using the acoustically-driven microfluidic extensional rheometry instrument, wherein the determination includes receiving thread thinning data of the tear sample obtained using the acoustically-driven microfluidic extensional rheometry instrument, and analysing the thread thinning data to determine the thread thinning dynamics, wherein the determined thread thinning dynamics comprise at least one extensional viscosity measurement of the tear sample;
      calculate at least one physical parameter value of the tear sample based at least in part on the at least one extensional viscosity measurement of the determined thread thinning dynamics of the tear sample;
      evaluate Dry Eye Disease based at least in part on the calculated at least one physical parameter value of the tear sample and by:
         comparing the at least one physical parameter value with one or more reference values for evaluating Dry Eye Disease, wherein the at least one physical parameter value is selected from the group consisting of: a surface/interface tension; a surface/interface viscosity; a surface/interface elasticity; a final break-up time; a relaxation time; and an extensional viscosity; and evaluating Dry Eye Disease based on the comparison of the at least one physical parameter value with the one or more reference values for evaluating Dry Eye Disease; and based on the comparison of the at least one physical parameter value with the one or more reference values for evaluating Dry Eye Disease, one or more of:

diagnose a presence of Dry Eye Disease;

assess a severity of Dry Eye Disease; and identify a clinical sub-type of Dry Eye Disease by classifying the clinical sub-type of Dry Eye Disease as one or both of aqueous deficient Dry Eye Disease and evaporative Dry Eye Disease, wherein one of:

the clinical sub-type is classified as aqueous deficient Dry Eye Disease when an extensional viscosity value of the tear sample is less than 0.00651 Pa·s, otherwise the clinical sub-type is classified as evaporative Dry Eye Disease, or the clinical sub-type is classified as aqueous deficient Dry Eye Disease when an extensional viscosity value of the tear sample is in the range of 0.00307 Pa·s to 0.0105 Pa·s and the clinical sub-type is classified as evaporative Dry Eye Disease when an extensional viscosity value of the tear sample is in the range of 0.00455 Pa·s to 0.0151 Pa·s.

20. The device of claim 19, wherein the thread thinning data includes changes in radius along a fluid capillary bridge of the tear sample during thread thinning, wherein the fluid capillary bridge is formed using the acoustically-driven microfluidic extensional rheometry instrument.

* * * * *